US012311036B2

(12) United States Patent
Rodriguez-Tanty et al.

(10) Patent No.: US 12,311,036 B2
(45) Date of Patent: May 27, 2025

(54) METAL OXIDES NANOPARTICLES CONJUGATED WITH NAPHTHALENE DERIVATIVES AS CONTRAST AGENTS FOR THE DETECTION OF BETA AMYLOID PLAQUES BY MAGNETIC RESONANCE IMAGES

(71) Applicants: CENTRO DE NEUROCIENCIAS DE CUBA, Havana (CU); FACULTAD DE QUÍMICA UNIVERSIDAD DE LA HABANA, Havana (CU)

(72) Inventors: Chryslaine Rodriguez-Tanty, Havana (CU); Marquiza Sablón Carrazana, Havana (CU); Evelio González Dalmau, Havana (CU); Alicia Marcelina Díaz García, Havana (CU); Armando Augusto Paneque Quevedo, Havana (CU); Andy Guzmán Rodríguez, Havana (CU); Julio Ricardo Rodríguez Izquierdo, Havana (CU); Suchitil Rivera Marrero, Havana (CU); Armando José Hernández Rodríguez, Artemisa (CU); Israel Reyes Molina, Havana (CU); Claudia Iriarte Mesa, Havana (CU); Samila León Chaviano, Havana (CU); Roberto Soto Menéndez Del Valle, Havana (CU); Alberto Bencomo Martínez, Artemisa (CU)

(73) Assignees: Centro De Neurociencias De Cuba, Havana (CU); Facultad De Quimica Universidad De La Habana, Havana (CU)

( * ) Notice: Subject to any disclaimer, the term of this patent is extended or adjusted under 35 U.S.C. 154(b) by 926 days.

(21) Appl. No.: 17/291,996

(22) PCT Filed: May 13, 2019

(86) PCT No.: PCT/CU2019/050005
§ 371 (c)(1),
(2) Date: May 6, 2021

(87) PCT Pub. No.: WO2020/094161
PCT Pub. Date: May 14, 2020

(65) Prior Publication Data
US 2021/0290782 A1 Sep. 23, 2021

(30) Foreign Application Priority Data
Nov. 6, 2018 (CU) .................. 2018-0138

(51) Int. Cl.
*A61K 49/18* (2006.01)
*B82Y 5/00* (2011.01)
*B82Y 30/00* (2011.01)
*B82Y 40/00* (2011.01)

(52) U.S. Cl.
CPC ............ *A61K 49/186* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| 9,764,047 B2* | 9/2017 | Sablón Carrazana ................. A61K 51/0402 |
| 2003/0147811 A1* | 8/2003 | Wisniewski ......... A61K 49/085 424/9.34 |
| 2011/0171715 A1* | 7/2011 | Chang ................. A61K 49/186 977/773 |
| 2012/0321560 A1 | 12/2012 | Carrazana et al. |

FOREIGN PATENT DOCUMENTS

| CA | 2789869 A1 | 10/2010 |
| CU | 20100204 A7 | 6/2012 |
| EP | 2436666 A2 | 4/2012 |
| EP | 2860169 A2 | 4/2015 |
| WO | 2010118706 A2 | 10/2020 |
| ZA | 2012/07005 | 1/2014 |

OTHER PUBLICATIONS

Cheng et al (Curcumin-conjugated magnetic nanoparticles for detecting amyloid plaques in Alzheimer's disease mice using magnetic resonance imaging (MRI). Biomaterials 44 (2015) 155-172) (Year: 2015).*
Gong, Yuesong, et al. "Alzheimer's Disease-Affected Brain: Presence of Oligomeric Aβ Ligands (ADDLs) Suggests a Molecular Basis for Reversible Memory Loss," Proceedings of the National Academy of Sciences, vol. 100, No. 18, pp. 10417-10422 (2003).
Scheuner, D., et al. "Secreted Amyloid β-Protein Similar to that in the Senile Plaques of Alzheimer's Disease is Increased in Vivo by the Presenilin 1 and 2 and APP Mutations Linked to Familial Alzheimer's Disease," Nature Medicine, vol. 2, No. 8 pp. 864-870 (1996).

(Continued)

Primary Examiner — Jake M Vu
(74) Attorney, Agent, or Firm — Hoffmann & Baron LLP

(57) ABSTRACT

Compounds with magnetic properties are provided herein, which belong to the category of metal oxide nanoparticles, coated and conveniently functionalized, which are conjugated with naphthalene compounds related to agglomerates and β-amyloid plaques present in neurodegenerative diseases. These new nanoparticles (NPs) are used for the non-invasive detection of agglomerates and amyloid plaques using the Magnetic Resonance Imaging (MRI) technique. The nanoparticles described here cross the blood-brain barrier (BBB), without the use of any membrane-disrupting agent. Likewise, they bind with high affinity and specificity to the agglomerates and β-amyloid plaques, and are used as contrast agents in MRI for the early detection of Alzheimer's disease (AD).

4 Claims, 27 Drawing Sheets

(56) References Cited

OTHER PUBLICATIONS

Dekosky, Steven T., et al., "Looking Backward to Move Forward: Early Detection of Neurodegenerative Disorders," Science, vol. 302.5646 pp. 830-834 (2003).

Monsonego, Alon, et al., "Immunotherapeutic Approaches to Alzheimer's Disease," Science, vol. 302.5646 pp. 834-838 (2003).

Wolk, David A., et al., "Update on Amyloid Imaging: from Healthy Aging to Alzheimer's Disease." Current Neurology and Neuroscience Reports, vol. 9, No. 5, pp. 345-352 (2009).

Klunk, W. E. "Biological Markers of Alzheimer's Disease," Neurobiology of Aging, vol. 19, No. 2 pp. 145-147 (1998).

Higuchi, Makoto, et al.,. "19 F and 1 H MRI Detection of Amyloid β Plaques in Vivo," Nature Neuroscience, vol. 8, No. 4, pp. 527-533 (2005).

Ter-Pogossian M.M. "Positron Emission Tomography (PET)," In Diagnostic Imaging in Medicine, pp. 273-377, Springer, Dordrecht (1983), https://doi.org/10.1007/978-94-009-6810-3_12.

Wagner, Anja, et al. "Contrast-Enhanced MRI and Routine Single Photon Emission Computed Tomography (SPECT) Perfusion Imaging for Detection of Subendocardial Myocardial Infarcts: An Imaging Study," The Lancet vol. 361, pp. 374-379 (2003).

Catafau, Ana M., et al., "Amyloid PET Imaging: Applications Beyond Alzheimer's Disease," Clinical and Translational Imaging, vol. 3, No. 1, pp. 39-55 (2015).

Furumoto, Shozo, et al. "Recent Advances in the Development of Amyloid Imaging Agents," Current Topics in Medicinal Chemistry, vol. 7, No. 18, pp. 1773-1789 (2007).

Klunk, William E., et al. "Imaging Brain Amyloid in Alzheimer's Disease with Pittsburgh Compound-B," Annals of Neurology: Official Journal of the American Neurological Association and the Child Neurology Society, vol. 55, No. 3, pp. 306-319 (2004).

Nordberg, Agneta, "PET Imaging of Amyloid in Alzheimer's Disease," The Lancet Neurology, vol. 3, No. 9, pp. 519-527 (2004).

Choi, Seok Rye, et al. "Preclinical Properties of 18F-AV-45: A PET Agent for Aβ Plaques in the Brain," Journal of Nuclear Medicine, vol. 50, No. 11, pp. 1887-1894 (2009).

Kung, Hank F., et al. "18F Stilbenes and Styrylpyridines for PET Imaging of Aβ Plaques in Alzheimer's Disease: A Miniperspective," Journal of Medicinal Chemistry, vol. 53, No. 3, pp. 933-941 (2010).

Rowe, Christopher C., et al. "Head-to-Head Comparison of 11C-PiB and 18F-AZD4694 (NAV4694) for β-amyloid Imaging in Aging and Dementia," Journal of Nuclear Medicine, vol. 54, No. 6, pp. 880-886 (2013).

Cselényi Zsolt, et al. "Clinical Validation of 18F-AZD4694, an Amyloid-β-Specific PET Radioligand," Journal of Nuclear Medicine, vol. 53, No. 3, pp. 415-424 (2012).

Salerno, Milena, et al., "Alzheimer's Disease: The Use of Contrast Agents for Magnetic Resonance Imaging to Detect Amyloid Beta Peptide Inside the Brain," Coordination Chemistry Reviews, vol. 327, pp. 27-34 (2016).

De Lartigue, Jane, "Flutemetamol (18F): A β-amyloid Positron Emission Tomography Tracer for Alzheimer's and Dementia Diagnosis," Drugs of Today (Barcelona, Spain: 1998), vol. 50, No. 3, pp. 219-229 (2014).

Villemagne, Victor L., et al. "Amyloid Imaging with 18F-Florbetaben in Alzheimer Disease and Other Dementias," Journal of Nuclear Medicine, vol. 52, No. 8, pp. 1210-1217 (2011).

Habte, F., et al. "Effects of System Geometry and Other Physical Factors on Photon Sensitivity of High-Resolution Positron Emission Tomography," Physics in Medicine & Biology, vol. 52, No. 13, pp. 3753-3772 (2007).

Alzheimer's Disease Facts and Figures 2018. "Alzheimer's Association," Alzheimer's & Dementia, vol. 14, No. 3, pp. 367-429 (2018)(Part1-3).

Borroni, Barbara, et al., "Predicting Alzheimer Dementia in Mild Cognitive Impairment Patients: Are Biomarkers Useful?," European Journal of Pharmacology, vol. 545, No. 1, pp. 73-80 (2006).

Mier, Walter, et al., "Advantages in Functional Imaging of the Brain," Frontiers in Human Neuroscience, vol. 9 Article 249 (2015).

Azria, David, et al. "Nanoparticles as Contrast Agents for Brain Nuclear Magnetic Resonance Imaging in Alzheimer's Disease Diagnosis," Journal of Materials Chemistry B, vol. 5, No. 35, pp. 7216-7237 (2017)(Part1-2).

Shokrollahi, H., et al., "Magnetic Resonance Imaging by Using Nano-Magnetic Particles," Journal of Magnetism and Magnetic Materials, vol. 369, pp. 176-183 (2017).

Felton, Charlette, et al. "Magnetic Nanoparticles as Contrast Agents in Biomedical Imaging: Recent Advances in Iron-and Manganese-Based Magnetic Nanoparticles," Drug Metabolism Reviews, vol. 46, No. 2, pp. 142-154 (2014).

Pierre, Valérie, C., et al., "Contrast Agents for MRI: 30+ Years and Where are We Going?" (J Biol Inorg Chem, vol. 19, pp. 127-131 (2014). DOI 10.1007/s00775-013-1074-5.

Caravan, Peter, et al. "Gadolinium (III) Chelates as MRI Contrast Agents: Structure, Dynamics, and Applications," Chemical Reviews, vol. 99, No. 9, pp. 2293-2352 (1999)(Part1-3).

Burtea, Carmen, et al. "Contrast Agents: Magnetic Resonance," Molecular Imaging I, Handbook of Experimental Pharmacology, pp. 135-165 (Springer-Verlag, Berlin Heidelberg 2008).

Ahrén, Maria, et al., "A Simple Polyol-Free Synthesis Route to Gd-2-O-3 Nanoparticles for MRI Applications: An Experimental and Theoretical Study," Journal of Nanoparticle Research, vol. 14:1006 (2012).

Faucher, Luc, et al. "Rapid Synthesis of PEGylated Ultrasmall Gadolinium Oxide Nanoparticles for Cell Labeling and Tracking with MRI," ACS Applied Materials & interfaces, vol. 4, No. 9, pp. 4506-4515 (2012).

Rohrer, Martin, et al. "Comparison of Magnetic Properties of MRI Contrast Media Solutions at Different Magnetic Field Strengths," Investigative Radiology, vol. 40, No. 11, pp. 715-724 (2005).

Port, Marc, et al. "Efficiency, Thermodynamic and Kinetic Stability of Marketed Gadolinium Chelates and their Possible Clinical Consequences: A Critical Review," Biometals, vol. 21, No. 4, pp. 469-490 (2008).

Frullano, Luca, et al., "Strategies for the Preparation of Bifunctional Gadolinium (III) Chelators," Current Organic Synthesis, vol. 8, No. 4, pp. 535-565 (2011)(Part1-2).

Grobner, Thomas, "Gadolinium—A Specific Trigger for the Development of Nephrogenic Fibrosing Dermopathy and Nephrogenic Systemic Fibrosis?" Nephrology Dialysis Transplantation, vol. 21, No. 4, pp. 1104-1108 (2006).

Bort, Guillaume, et al. "Gadolinium-Based Contrast Agents Targeted to Amyloid Aggregates for the Early Diagnosis of Alzheimer's Disease by MRI," European Journal of Medicinal Chemistry, vol. 87, pp. 843-861 (2014).

Caravan, Peter. "Strategies for Increasing the Sensitivity of Gadolinium Based MRI Contrast Agents," Chemical Society Reviews, vol. 35, No. 6, pp. 512-523 (2006).

Sillerud, Laurel O., et al., "SPION-Enhanced Magnetic Resonance Imaging of Alzheimer's Disease Plaques in AβPP/PS-1 Transgenic Mouse Brain," Journal of Alzheimer's Disease, vol. 34, No. 2, pp. 349-365 (2013).

Wadghiri, Youssef Zaim, et al. "Detection of Alzheimer's Amyloid in Transgenic Mice Using Magnetic Resonance Microimaging," Magnetic Resonance in Medicine: An Official Journal of the International Society for Magnetic Resonance in Medicine, vol. 50, No. 2, pp. 293-302 (2003).

McCarty, D. M., et al., "Mannitol-Facilitated CNS Entry of rAAV2 Vector Significantly Delayed the Neurological Disease Progression in MPS IIIB Mice," Gene Therapy, vol. 16, No. 11, pp. 1340-1352 (2009).

Poduslo, Joseph F., et al., "In Vivo Targeting of Antibody Fragments to the Nervous System for Alzheimer's Disease Immunotherapy and Molecular Imaging of Amyloid Plaques," Journal of Neurochemistry, vol. 102, No. 2, pp. 420-433 (2007).

Xu, Chenjie, et al., "New Forms of Superparamagnetic Nanoparticles for Biomedical Applications," Advanced Drug Delivery Reviews, vol. 65, No. 5, pp. 732-743 (2013).

Sigurdsson, Einar M., et al., "A Non-Toxic Ligand for Voxel-Based MRI Analysis of Plaques in AD Transgenic Mice," Neurobiology of Aging, vol. 29, No. 6, pp. 836-847 (2008).

(56) References Cited

OTHER PUBLICATIONS

Yang, Jing, et al., "Detection of Amyloid Plaques Targeted by USPIO-Aβ1-42 in Alzheimer's Disease Transgenic Mice Using Magnetic Resonance Microimaging," Neuroimage, vol. 55, No. 4, pp. 1600-1609 (2011).
Häfeli, Urs O., et al., "Cell Uptake and in Vitro Toxicity of Magnetic Nanoparticles Suitable for Drug Delivery," Molecular Pharmaceutics, vol. 6, No. 5, pp. 1417-1428 (2009).
Jeng, Hueiwang Anna, et al., "Toxicity of Metal Oxide Nanoparticles in Mammalian Cells," Journal of Environmental Science and Health Part A 41.12, pp. 2699-2711 (2006).
Ku, Shuting, et al. "The Blood-Brain Barrier Penetration and Distribution of PEGylated Fluorescein-Doped Magnetic Silica Nanoparticles in Rat Brain," Biochemical and Biophysical Research Communications, vol. 394, No. 4, pp. 871-876 (2010).
Howard, Melissa D., et al. "PEGylation of Nanocarrier Drug Delivery Systems: State of the Art," Journal of Biomedical Nanotechnology, vol. 4, No. 2, pp. 133-148 (2008).
Wadghiri, Youssef Zaim, et al. "Detection of Amyloid Plaques Targeted by Bifunctional USPIO in Alzheimer's Disease Transgenic Mice Using Magnetic Resonance Microimaging," PloS one, vol. 8, No. 2, e57097 (2013).
Zhang, D., et al. "The Detection of β-amyloid Plaques in an Alzheimer's Disease Rat Model with DDNP-SPIO." Clinical Radiology, vol. 70, No. 1, pp. 74-80 (2015).
Nordberg, Agneta, "Amyloid Imaging in Alzheimer's Disease," Current Opinion in Neurology, vol. 20, No. 4, pp. 398-402 (2007).
Henriksen, Gjermund, et al., "Development and Evaluation of Compounds for Imaging of β-amyloid Plaque by Means of Positron Emission Tomography," European Journal of Nuclear Medicine and Molecular Imaging, vol. 35, No. 1, pp. 75-81 (2008).
Tolboom, Nelleke, et al., "Molecular Imaging in the Diagnosis of Alzheimer's Disease: Visual Assessment of [11C] PIB and [18F] FDDNP PET Images," Journal of Neurology, Neurosurgery & Psychiatry, vol. 81, No. 8, pp. 882-884 (2010).
Cheng, Kwok Kin, et al., "Curcumin-Conjugated Magnetic Nanoparticles for Detecting Amyloid Plaques in Alzheimer's Disease Mice Using Magnetic Resonance Imaging (MRI)," Biomaterials, vol. 44, pp. 155-172 (2015).
Kouyoumdjian, Hovig, et al., "Glyconanoparticle Aided Detection of β-amyloid by Magnetic Resonance Imaging and Attenuation of β-amyloid Induced Cytotoxicity," ACS Chemical Neuroscience, vol. 4, No. 4, pp. 575-584 (2013).
Lu, An-Hui, E., et al., "Magnetic Nanoparticles: Synthesis, Protection, Functionalization, and Application," Angewandte Chemie International Edition, vol. 46, No. 8, pp. 1222-1244 (2007). DOI: 10.1002/anie.200602866.
Zheng, Yuan-Hui, et al. "Synthesis and Magnetic Properties of Fe3O4 Nanoparticles," Materials Research Bulletin, vol. 41, Issue. 3, pp. 525-529 (2006).
Hyeon, Taeghwan, et al. "Synthesis of Highly Crystalline and Monodisperse Maghemite Nanocrystallites Without a Size-Selection Process," Journal of the American Chemical Society, vol. 123, No. 51, pp. 12798-12801 (2001).
Bautista, M. Carmen, et al. "Surface Characterisation of Dextran-Coated Iron Oxide Nanoparticles Prepared by Laser Pyrolysis and Coprecipitation," Journal of Magnetism and Magnetic Materials, vol. 293, No. 1, pp. 20-27 (2005).
Gayathri, Thirumalraj, et al.,"Gadolinium Oxide Nanoparticles for Magnetic Resonance Imaging and Cancer Theranostics," Journal of Bionanoscience, vol. 9, No. 6, pp. 409-423 (2015).
Liu, Yongjun, et al., "Gadolinium Loaded Nanoparticles in Theranostic Magnetic Resonance Imaging," Biomaterials, vol. 33, No. 21, pp. 5363-5375 (2012).
Tokumitsu, Hiroyuki, et al. "Preparation of Gadopentetic Acid-Loaded Chitosan Microparticles for Gadolinium Neutron-Capture Therapy of Cancer by a Novel Emlsion-Droplet Coalescence Technique," Chemical and Pharmaceutical Bulletin, vol. 47, No. 6, pp. 838-842 (1999).
McDonald, Michael Alexander, et al., "Investigations into the Physicochemical Properties of Dextran Small Particulate Gadolinium Oxide Nanoparticles," Academic Radiology, vol. 13, No. 4, pp. 421-427 (2006).
Wyrzykowska, Ewelina, et al. "Development of a Novel in Silico Model of Zeta Potential for Metal Oxide Nanoparticles: A Nano-QSPR Approach," Nanotechnology, vol. 27, No. 44, p. 445702 (2016).
Chen, Zhongjing, et al, "Structure and Orientation of Peptide Inhibitors Bound to Beta-Amyloid Fibrils," Journal of Molecular Biology, vol. 354, No. 4, pp. 760-776 (2005).
Landau, Meytal, et al. "Towards a pharmacophore for amyloid." PLoS biology 9.6 (2011): e1001080.
Hetényi, Csaba, et al. "Pentapeptide Amides Interfere with the Aggregation of β-amyloid Peptide of Alzheimer's Disease." Biochemical and Biophysical Research Communications, vol. 292, No. 4., pp. 931-936 (2002).
Xia, Ning, et al., "Probing of EDC/NHSS-Mediated Covalent Coupling Reaction by the Imobilization of Electrochemically Active Biomolecules," Int. J. Electrochem. Sci., vol. 8, pp. 2459-2467 (2013).
Fanea, Laura, et al., "Relaxation Times Mapping Using Magnetic Resonance Imaging," Romanian Report in Physics, vol. 63, No. 2, pp. 456-464 (2011).
Epstein, Charles L., et al., "Magnetic Resonance Imaging", Jun. 3, 2005.
Reimer, Peter, et al., "Ferucarbotran (Resovist): A New Clinically Approved RES-Specific Contrast Agent for Contrast-Enhanced MRI of the Liver: Properties, Clinical Development, and Applications." European Radiology, vol. 13, No. 6, pp. 1266-1276 (2003).
Levy, Michael, et al. "Long Term in Vivo Biotransformation of Iron Oxide Nanoparticles," Biomaterials, vol. 32, No. 16, pp. 3988-3999 (2011).
Salafranca, Juan, et al. "Surfactant Organic Molecules Restore Magnetism in Metal-Oxide Nanoparticle Surfaces," Nano Letters, vol. 12, No. 5, pp. 2499-2503 (2012).
Elster, Allen D., et al., "Pseudolayering of Gd-DTPA in the Urinary Bladder," Radiology, vol. 174, No. 2, pp. 379-381 (1990).
Zhou, Jingting, et al. "Synthesis of Superparamagnetic Iron Oxide Nanoparticles Coated with a DDNP-Carboxyl Derivative for in Vitro Magnetic Resonance Imaging of Alzheimer's Disease," Materials Science and Engineering: C 37, pp. 348-355 (2014).
Choi, Seok Rye, et al. "Correlation of Amyloid PET Ligand Florbetapir F 18 (18F-AV-45) Binding with β-amyloid Aggregation and Neuritic Plaque Deposition in Postmortem Brain Tissue," Alzheimer Disease and Associated Disorders, vol. 26, No. 1, pp. 8-16 (2012).
Tu, Peiyu, et al., "Compounds for Imaging Amyloid-β Deposits in an Alzheimer's Brain: A Patent Review," Expert Opinion on Therapeutic Patents, vol. 25.4 (2015): 413-423.
Lührs, Thorsten, et al. "3D Structure of Alzheimer's Amyloid-β (1-42) Fibrils," Proceedings of the National Academy of Sciences, vol. 102, No. 48, pp. 17342-17347 (2005).
Yang, Chang-Tong, et al., "Gd (III) Chelates for MRI Contrast Agents: From High Relaxivity to "Smart", From Blood Pool to Blood-Brain Barrier Permeable," Med. Chem. Comm., vol. 3, No. 5, pp. 552-565 (2012).
Martinez-Lorca Alberto, et al. "Aportación de la Imagen Molecular en la Exploración del Cerebro," Revista de Neurologia, vol. 64, p. 480 (2017). (Google translation attached "Contribution of Molecular Imaging in Brain Exploration").
Zhou, Zhuxian, et al, "Gadolinium-Based Contrast Agents for Magnetic Resonance Cancer Imaging," Wiley Interdisciplinary Reviews: Nanomedicine and Nanobiotechnology, vol. 5, No. 1, pp. 1-18 (2013).
Poduslo, Joseph F., et al. "Molecular Targeting of Alzheimer's Amyloid Plaques for Contrast-Enhanced Magnetic Resonance Imaging, " Neurobiology of Disease, vol. 11, No. 2, pp. 315-329 (2002).
Ahmad, MD. Wasi, et al. "Bovine Serum Albumin (BSA) and Cleaved-BSA Conjugated Ultrasmall Gd2O3 Nanoparticles: Synthesis, Characterization, and Application to MRI Contrast Agents," Colloids and Surfaces A: Physicochemical and Engineering Aspects, vol. 450, pp. 67-75 (2014).

(56) References Cited

OTHER PUBLICATIONS

Pati, S. S., et al. "High Temperature Phase Transformation Studies in Magnetite Nanoparticles Doped with Co2+ Ion," Journal of Applied Physics, vol. 112, No. 5, p. 054320 (2012).

Lawrence, M. Jayne, et al., "Microemulsion-Based Media as Novel Drug Delivery Systems," Advanced Drug Delivery Reviews, vol. 64, pp. 175-193 (2012).

Brown, Robert W., et al. "Magnetic Resonance Imaging: Physical Principles and Sequence Design," John Wiley & Sons, 2014. (relevant pages).

Verhoeff, Nicolaas Plg, et al. "Amyloid Imaging with [11C] SB-13 PET: A Test-Retest Reliability Study," Alzheimer's and Dementia, vol. 6, No. 4, p. 2 (2010).

Poduslo, Joseph F., et al. "Design and Chemical Synthesis of a Magnetic Resonance Contrast Agent with Enhanced in Vitro Binding, High Blood-Brain Barrier Permeability, and in Vivo Targeting to Alzheimer's Disease Amyloid Plaques," Biochemistry, vol. 43, No. 20, pp. 6064-6075 (2004).

Yang, Che-Chaun, et al. "Biofunctionalized Magnetic Nanoparticles for Specifically Detecting Biomarkers of Alzheimer's Disease in Vitro," ACS Chemical Neuroscience, vol. 2, No. 9, pp. 500-505 (2011).

Heurling, Kerstin, et al. "Imaging β-amyloid Using [18 F] Flutemetamol Positron Emission Tomography: From Dosimetry to Clinical Diagnosis," European Journal of Nuclear Medicine and Molecular Imaging, vol. 43, No. 2, pp. 362-373 (2016).

Singh, N., et al. "Potential Toxicity of Superparamagnetic Iron Oxide Nanoparticles (SPION). Nano Rev 1: 5358." (2010). 1:10. 3402/nano.v1i0.5358.

Skaat, Hadas, et al. "Antibody-Conjugated, Dual-Modal, Near-Infrared Fluorescent Iron Oxide Nanoparticles for Antiamyloidgenic Activity and Specific Detection of Amyloid-β Fibrils," International Journal of Nanomedicine, vol. 8, pp. 4063 (2013).

Viola, Kirsten L., et al. "Towards Non-Invasive Diagnostic Imaging of Early-Stage Alzheimer's Disease," Nature Nanotechnology, vol. 10, No. 1, pp. 91-98 (2015).

* cited by examiner

| Measurements | Diameter (nm) |
|---|---|
| 1 | 10.1 |
| 2 | 10.3 |
| 3 | 14.1 |
| 4 | 9.4 |
| 5 | 12.3 |
| 6 | 10.5 |
| Mean | 11.1±1.8 |

FIG. 4B

METAL OXIDES NANOPARTICLES CONJUGATED WITH NAPHTHALENE DERIVATIVES AS CONTRAST AGENTS FOR THE DETECTION OF BETA AMYLOID PLAQUES BY MAGNETIC RESONANCE IMAGES

CROSS-REFERENCE TO RELATED APPLICATIONS

This application is the U.S. National Phase of International Patent Application Number PCT/CU2019/050005 filed 13 May 2019, which claims priority from CU 2018-0138 filed 6 Nov. 2018, each of which is incorporated herein by reference.

BACKGROUND OF THE INVENTION

AD is a neurodegenerative disorder that leads to the loss of cognitive abilities and memory, disorientation, language disorders and behavior changes; problems that worsen rapidly and progressively over time, and adversely affects the quality of life of patients. It comprises 60 to 80 percent of cases of dementia and is among the six conditions listed by the World Health Organization (WHO).

The neuropathological characteristics of AD are due to the presence of protein deposits in the brain: neurofibrillary tangles (NFT) and senile plaques (SP), which are involved in the process that leads to progressive neuronal degeneration and neuronal death. SP are composed by deposits of β-amyloid peptides of 39-42 amino acids, while NFTs are produced by hyperphosphorylation of the tau protein (Gong et al., in Proceedings of the National Academy of Sciences, 2003, 100 (18), 10417-10422 and Scheuner et al., in Nature Medicine, 1996, 2 (8), 864.2, 3).

The β-amyloid peptides deposits appear up to 20 years before the symptoms of this disease manifest; therefore, they are considered a therapeutic target. It is also known that the implementation of early therapy can delay the onset of the manifestation of AD and decrease its prevalence, so its early diagnosis is vitally important (DeKosky, in Science, 2003: 830-834 and Monsonego, in Science, 2003, 834-838).

The clinical diagnosis of AD has a moderate reliability and frequently lacks adequate sensitivity and specificity (Wolk et Klunk, in Current Neurology and Neuroscience Reports 2009, 9 (5), 345-352). It is accurate only when is performed post mortem, through the visualization of pathological structures with specific staining agents such as Congo Red, Chrisamine-G or Thioflavin-T (Klunk, in Neurobiology of Aging, 1998, 19 (2), 145-147).

In order to develop non-invasive methods for the detection of β-amyloid plaques and diagnose AD in early stages, traditional neuroimaging techniques have been used with greater or lesser success: Magnetic Resonance Imaging (MRI) (Higuchi et al., in Nature Neuroscience, 2005, 8 (4): 527), Positron Emission Tomography (PET) (Ter-Pogossian, in Diagnostic Imaging in Medicine, 1983, Springer, 273-277) and Single Photon Emission Computed Tomography (SPECT) (Wagner et al., in The Lancet, 2003, 361 (9355): 374-379). For this purpose, many compounds have been used for the in vivo labeling of neuropathological structures in the imaging molecular tests.

Some compounds labeled with positron-emitting radionuclides have been studied as radiopharmaceuticals for the detection of SP in patients with AD (Catafau et al in Clin Transl Imaging 2015; 3: 39-55), such as: styrylbenzene, benzothiazole, stilbene, vinylbenzoxazole, naphthalene derivatives and others (Furumoto et al., in Curr Top Med Chem 2007; 7: 1773-1789). Examples thereof are: 2-(4'-[$^{11}$C]methylaminophenyl)-6-hydroxybenzothiazole ([$^{11}$C] PIB) (Klunk et al., in Ann Neurol., 2004; 55: 306-319), 2-(1-{6-[(2 [$^{18}$F]-fluoroethyl) (methyl)-amino]2-naphthyl}ethyl-dene)-malononitrile ([$^{18}$F]FDDNP) (Nordberg, in Lancet Neurol., 2004; 3: 519-527), 4-N-[$^{11}$C]methylamino-4'-hydroxystilbene (SB-13) (Verhoeff et al., in Am J Geriatr Psychiatry 2004; 12: 584), 4-[(E)-2-(6-{2-[2-(2-[$^{18}$F]fluoroethoxy)-ethoxy]ethoxy}pyridine-3-yl) vinyl]-N-methylaniline ([$^{18}$F]AV-45) (Choi et al., in J. Nucl Med. 2009; 50: 1887-1894), 4-[(E)-2-(4-{2-[2-(2-[$^{18}$F]fluoroethoxy) ethoxy]ethoxy}phenyl) vinyl]-N-methylaniline ([$^{18}$F] BAY94-9172) (Kung et al., in J Med Chem 2010; 53: 933-941), 2-[3-[$^{18}$F]fluoro-4-(methylamino)phenyl]-1,3-benzothiazol-6-ol ([$^{18}$F]GE-067) (Kung et al., in J Med Chem 2010; 53: 933-941) and 2-(2-[$^{18}$F]fluoro-6-(methylamino) pyridin-3-yl) benzofuran-6-ol ([$^{18}$F]AZD4694) (Rowe et al., in J. Nucl Med. 2013; 54: 880-886; Cselényi et al., in J. Nucl Med. 2012; 53: 415-424). In general, radiotracers must have specific properties to be used for the in vivo detection of AB plaques. For example, they should have a high binding affinity in vitro (Ki<10 nM), a high permeability through the BBB (log P<3), a high initial brain uptake with rapid clearance in the normal brain, and should also have a high specific to nonspecific binding ratio in the brain (Salerno et al., in Coordination Chemistry Reviews 2016; 327: 27-34). In addition, the labelling procedures must be efficient (Kung et al in J Med Chem 2010; 53: 933-941). In the last five years, the US Food and Drug Administration (FDA) has approved the use of three of the compounds mentioned above: [18F]Florbetapir ([$^{18}$F]AV-45, Amyvid, 2012) (Choi, et al., in Alzheimer Dis. Assoc Disord 2012; 26: 8), [$^{18}$F]Flutemetamol ([$^{18}$F]GE-067, Vizamyl, 2013) (Lartigue et al., in Drugs Today 2014; 50: 219-229) and [$^{18}$F]Florbetaben ([$^{18}$F]BAY94-9172, Neuraceq, 2014) (Villemagne et al., in J. Nucl Med. 2011; 52: 1210-1217) as PET radiopharmaceuticals for visualization of deposits of Aβ plaques in brains of AD patient's. However, most of the probes labeled with $^{18}$F— have a high non-specific binding to the white matter of the brain, both in healthy subjects and those suffering from Alzheimer's, which decreases in the accurate diagnosis in the early stages of the disease (Tu et al., in Expert Opin. Ther. Patents, 2015, 25 (4), doi 10.1517% 2F13543776.2015.1007953). In addition, the PET technique has as disadvantages its low spatial resolution and its invasiveness due to the use of radiotracers (Habte et al in Phys. Med. Biol. 2007, 52, 3753-3772). Also, these probes are very expensive and require rapid access to cyclotrons, so they are mainly limited to research (Alzheimer's Association, Alzheimer & Dement, 2018, 14, 367-429).

In the case of the SPECT technique, the radiopharmaceutical most commonly used to obtain neuroimaging is $^{99m}$Tc-HMPAO ($^{99}$mTc-hexamethylpropylene-oxime). This compound, with lipophilic characteristics, rapidly crosses the BBB and is used in brain perfusion studies to characterize the reduction of blood flow in certain regions of the brain, what is evidenced in brain diseases, as well as in the early stages of AD (Borroni et al in European Journal of Pharmacology 2006, 545 (1), 73-80). However, this radiopharmaceutical is not related to SP or NFT, so the precise diagnosis of this disease is not possible, without that so far there is another suitable radiopharmaceutical. (Tu et al., in Expert Opin. Ther. Patents, 2015, 25 (4)). On the other hand, this technique presents another great disadvantage, and it is its low spatial resolution that does not allow the visualization of microscopic structures in the brain.

The use of MRI in clinical practice allows obtaining information, in a non-invasive way and without emitting ionizing radiation, from the different anatomical structures, better than other radiology tests. The use of this technique for the diagnosis of AD is useful as a first step to rule out other brain injuries. The studies carried out through MRI indicate that one of the first morphological alterations that occur is the reduction of the volume of the temporal lobes and, especially, the atrophy of the hippocampus. This correlates with the neuropathological processes that lead to memory loss in early stages of the disease, so the determination of the volume of the hippocampal region provides useful information for an early diagnosis of AD (Mier W et Mier D in Front Hum Neurosci 2015, 9: 249 and Azria D et al in J. Mater, Chem. B, 2017, 5 (35), 7216-7237). On the other hand, the images that are recorded have a higher spatio-temporal resolution, close to the microscopic one. Its main limitation in clinical practice is that it has low sensitivity and specificity for the identification of SP.

Higuchi et al. (in Nat Neurosci, 2005, 8 (4), 527-33) evaluated the use of (E,E)-1-fluoro-2,5-dis (3-hydroxycarbonyl-4-hydroxy) styrylbenzene as a probe related to amyloid plaques for visualization using $^{19}$F-MRI, with the aim of increasing the specificity of this technique. This compound was evaluated in transgenic mice of Alzheimer's disease, and although it was possible to acquire the image, the authors of this work consider that its application in humans will depend on the development of new hardware technologies (coil surface radio frequency receivers) and software for the MRI, in order to achieve a better specificity. In addition, they consider that the sensitivity of the SP detection is inadequate, since the number of fluorine atoms in the molecule is insufficient to obtain an optimal signal-to-noise ratio. Likewise, Sablón et al. (in US 20120321560 A1) propose the use of fluorinated naphthalene derivatives to be detected by MRI. However, this patent does not specify examples related to the use of these compounds and does not solve the sensitivity problems found in the state-of-the-art for the detection of amyloid plaques with the use of $^{19}$F probes for MRI.

The increase in detection sensitivity in the MRI can be solved with the use of contrast agents (CA) that allow the recording of higher contrast images. These compounds are defined as those substances that are introduced into the human body orally, nasally, subcutaneously, rectally, intracerebroventricularly or intravenously to improve the quality of the images. However, the development of these compounds for the diagnosis of neurodegenerative diseases is still an unresolved challenge in the current state of the art. The CAs described so far are not safe and effective, due to the problems related to their accumulation in the tissues, that is, their toxicity; its chemical stability and its capacity to cross the BBB (Azria D et al., in J. Mater, Chem. B, 2017, 5 (35), 7216-7237).

The MRI equipment for clinical use (0.2-3T), uses an intense magnetic field, with a pulsating field gradient, to study a region of interest, causing the polarization of the nuclear spins of $^1$H atoms in the direction of that field. When a specific radiofrequency pulse is applied, the protons absorb the energy and go into an excited state. When the excitation ceases, the protons relax by different mechanisms: spin reticulum (T1), emitting the energy they absorbed, and spin-spin (T2). The emitted energy, whose resonance frequencies depend on the geometric position of the $^1$H atoms, is detected by the scanner. Since the MRI signal has a multiparametric dependence with the appropriate selection of the excitation pulse sequence, we can obtain weighted images in T1, T2 or the diffusion of water protons (Shokrollahi, H., et al., in Journal of Magnetism and Magnetic Materials, 2014, 369: 126-183, 60 and Felton, C., et al., in Drug Metabolism Reviews, 2014. 46 (2): 142-154).

The relaxation times T1 and T2 are also modified with the use of CA that improve the sensitivity of the technique. The ideal CA is the one that manages to reach an adequate life time in the body to establish an exact diagnosis, with the least amount of adverse effects, being absorbed by the body and clearance by the urine or feces.

The CA decrease the relaxation times by different mechanisms. This leads to changes in the intensity of the pixel, increasing the contrast in the weighted images in T1 and T2 (Pierre V. C et al., in J. Biol. Inorg. Chem., 2014, 19, 127-131, Caravan, P et al., in Chem. Rev., 1999, 99, 2293-2352 and in Chem. Soc. Rev., 2006, 35, 512-523, Burtea, S. in Molecular Imaging I, Springer, Berlin, Heidelberg, 2008, 135-165).

The CAs are divided into:
  Positive contrast agent: Predominantly reduces the T1 of the tissue where it accumulates, producing an increase in tissue intensity in heavy images in T1. Gadolinium compounds are included in this category. (Gadovist, Magnevist) (Ahrén M, et al in Nanopart, Res. 2012, 14, 1; Faucher L., et al., in ACS Appl. Mater. Interfaces 2012, 4, 4506)
  Negative contrast agent: Predominantly reduces the T2 of the tissue where it accumulates, producing a decrease in tissue intensity in heavy images in T2. This category includes iron oxide nanoparticles (USPIO Resovist) (Rohrer, M. et al in Invest Radiol 2005; 40: 715-724).

Various requirements has been described in order to develop an adequate CA for AD diagnosis, through visualization of Aβ deposits by MRI. These CA must: (i) cross the BBB, (ii) label the Aβ agglomerates specifically, (iii) not be toxic, (iv) not metabolized during its retention in the patient's body and finally (v) be eliminated from the body (Cheng et al in Biomaterial 2015: 44: 155-172). The low capacity to cross the BBB and the insufficient internalization in the brain have been the main obstacles to the clinical use of CA in the MRI.

Among the most used CAs in the MRI are the compounds of Gd(III), due to their high paramagnetism, their favorable properties in terms of electronic relaxation, their efficient biodistribution, elimination and their relatively high stability and inertia both thermodynamically and kinetically (Port et al., in Biometals 2008, 21, 469-490, Frullano et al in Curr, Org Synth, 2011, 8, 535-565 and Zhou et al in Wiley Interdiscip, Rev. Nanomed, Nanobiotechnol, 2013, 5 (1), 1892-94). Gd(III) ions are toxic per se because they can easily replace calcium(II) ions in the body by having both similar ionic radios. The Gd(III) ions, at physiological pH, precipitate in the form of Gd hydroxide crystals, which can accumulate in the liver, spleen and bones, being very harmful to health. To avoid this, they are complexed with organic ligands that prevent their toxic release to the organism. The most used Gd(III) complexes in medicine are: Magnevist® (Gd (DTPA)), Dotarem® (Gd (DOTA)), Prohance® (Gd (HP-DO3A)) and Omniscan® (Gd (DTPA-BMA)). These complexes possess a high thermodynamic stability and kinetic inertness, in terms of metal dissociation, ligand exchange and transmetallation, all of which is necessary for the Gd(III) complexes to avoid their toxicity in vivo. However, their use in patients with chronic renal failure is contraindicated due to their slow elimination from the organism (Grobner in Nephrology Dialysis Transplantation 2006, 21 (4), 1104-1108).

These commercial Gd(III) complexes have also been evaluated in patients with AD for the detection of amyloid plaques in the brain (Bort et al in European Journal of Medicinal Chemistry 2014, 87, 843-861 and Caravan in Chemical Society Reviews 2006, 35 (6), 512-523). Thus, Poduslo et al. (in Journal of Neurochemistry 2002, 81 (s1), 60-63), conjugated the complex of Gd-diethylenetriaminepentaacetic acid (DTPA) to a modified Aβ peptide (1-40) to improve the passage of CA through BBB in AD transgenic mice. Although the feasibility of the experiment was demonstrated, long exploration times and a high magnetic field strength (>7 T) were required. This makes this method impractical since the current instrumentation of MRI in clinical practice operates between 1.5 and 3T (Sillerud et al in Journal of Alzheimer's Disease 2013, 34 (2), 349-365). A similar approach that includes the use of both Gd-DTPA complexes and monocrystalline iron oxide nanoparticles coupled to Aβ (1-40) peptides was proposed by Wadghiri et al. (in Magnetic Resonance in Medicine 2003, 50 (2), 293-302). In both cases, the administration of CA was required intra-carotid; as well as the use of mannitol to increase the osmotic pressure of medium and cause a temporary effect on the permeability of BBB, which facilitates the transition of the CA (Bort, G., in Eur. J. Med. Chem. 2014, 87, 843-861). Mannitol is a parenteral osmotic diuretic that should be used with caution in patients older than 60 years. In this age group, renal, cardiac and cerebral diseases are more frequent, so their use is contraindicated. Likewise, the effect of mannitol in rodents is of short duration (15 min in rodents) (McCarty D M et al in Gene Ther 2009, 16: 1340-1352) and is associated with some toxicity.

In other investigations focused on improving this transition, the use of Gd(III) complexes bound to: Aβ peptides (Poduslo et al in Journal of Neurochemistry 2007, 102 (2), 420-433, in Biochemistry 2004, 43 (20), 6064-6075, Yang et al., in Med. Chem. Comm. 2012, 3 (5), 552-565), anti-Aβ antibodies (Poduslo et al., in J. Neurochem., 2007, 102, 420-433; Xu et al in Advanced Drug Delivery Reviews 2013, 65 (5), 732-743) and macrocycles is proposed, but in all these studies the results are not satisfactory. Likewise, Sigurdsson et al. (in Neurobiol Aging, 2008, 29 (6): 836-47), in an attempt to increase the permeability through the BBB of the Gd-DPTA complex conjugated with Aβ, incorporated polylysine residues (K6) into the Aβ peptide (K6-Aβ-Gd-DPTA). However, the results were not satisfactory either, so they had to use mannitol. These authors also explored the introduction of putrescine in CA, but recognition of Aβ deposits was inefficient. Another drawback of this CA was its short half-life in plasma (3 minutes), which indicates its instability or rapid excretion.

Another alternative of CA focused to the Aβ plaques recognition are iron oxide NPs, whose surface can be conjugated with some molecule that binds selectively to the plaques. Thus, Wadghiri et al. (in Magnetic Resonance in Medicine 2003, 50 (2): 293-302) present monocrystalline iron oxide NPs, coupled to the Aβ peptide (1-40), capable of detecting Aβ plaques after permeabilizing the BBB. Also Yang et al. (in Neuroimage, 2011, 55 (4): 1600-1609) had to permeabilize the BBB when they used ultra-small superparamagnetic iron oxide NPs (USPION, 10-40 nm) functionalized with the Aβ peptide (1-42).

In another approach, Yang et al. (in ACS Chemical Neuroscience, 2011, 2 (9): 500-505) conjugated the USPION with antibodies against to Aβ (1-40) and Aβ (1-42), and demonstrated in vitro the possibility of labeling both peptides. The authors of this work suggest that these NPs can be used as a diagnostic agent for AD, through the detection of Aβ peptides in human plasma. This procedure is based on the reduction of the immunomagnetic signal of the NPs in samples from normal subjects and patients with AD, with the use of a quantum interference device (SQUID). Thus, they determine very low concentrations of Aβ aggregates in plasma; however, the diagnosis is not precise as it does not allow the localization of agglomerates and Aβ plaques in the brain. On the other hand, it has been described that these USPIONS can cross cell membranes, and interfere in cell metabolism resulting toxic (Hafeli et al in Mol Pharm 2009; 6: 1417-28; Jeng et al., In J Environ Sci Health A Tox Hazard Subst Environ Eng 2006; 41: 2699-711 and Singh et al in Nano Rev. 2010; 1:10.3402/nano.v1i0.5358).

Another anti-Aβ antibody, BAM10, was conjugated to the USPION surface to detect, ex vivo, Aβ plaques in rat brains by MRI (Skaat et al., in International Journal of Nanomedicine, 2013, 8: 4063). Sillerud et al. (in Journal of Alzheimer's disease, 2013, 34 (2): 349-365) reported that the USPION, conjugated to antibodies that recognize the amyloid precursor protein (APP), can cross the BBB, link to Aβ plaques and improve their contrast in the MRI. After injection of this CA, without the use of mannitol, APP/PS1 transgenic mice were sacrificed to obtain brain slices. The samples were analyzed in MRI of 9.4T, and it was observed that the evaluated USPION improved the negative contrast in comparison to the brain samples without treating with CA, which suggests that these NPs can cross the BBB. The sequence used was mASE (multiple Asymmetric Spin Echo). From this protocol, six echoes were individually reconstructed and the resulting image volumes, which indicate the presence of SP, were added to increase the signal-to-noise ratio. This method, which employs a 9.4T field, is only applicable to samples of ex vivo tissue. All this indicates that the sensitivity described is not attainable when it is desired to carry out the in vivo detection of SP. It also requires the use of a 9.4T field that goes beyond the limits, approved by regulatory bodies, for clinical use in humans.

Viola et al. (in Nat Nanotechnol 2015, 10(1): 91-8) synthesized a probe for MRI designated NU4MNS with affinity to Aβ oligomers, by conjugation of selective antibodies to Aβ oligomers with superparamagnetic nanoparticles. This probe is specific and sensitive, and can in vitro distinguish the pathological brain tissue of an AD transgenic animal from the controls, by means of MRI. According to the ex vivo and in vivo results, the probe which is administered intranasally, crosses the BBB and remains in the brain tissue for more than 4 days, observing the presence of Aβ plaques. This prolonged time suggests an inadequate clearance, which could cause toxic effects.

Ku et al. (in Biochemical and Biophysical Research Communications 2010, 394, 871-876) and Howard et al. (in Journal of Biomedical Nanotechnology 2008, 4, 133-148) present the synthesis of USPION coated with polyethylene glycol (PEG). This type of coating inhibits the uptake of NPs by the reticuloendothelial system and prolongs their circulation, thus allowing access to the central nervous system. Other researchers have used this approach to increase the passage of USPION through the BBB and visualize in vivo the Aβ plaques in transgenic mice. However, the specificity in the detection of Aβ plaques has not been demonstrated. Thus, Wadghiri et al. (in PLoS One 2013; 8 (2): e57097) used NPs of the type USPIO-PEG-Aβ (1-42) for the detection of plaques in the brain of transgenic mice.

In this work, it is declared the obtaining of false positives by MRI in healthy animals. They also stated that they fail to correlate the obtained results from the in vivo detection of Aβ plaques by MRI with immunohistochemical assays.

Several studies have tried the conjugation of USPION with compounds of low molecular weight, based on the use of classic dyes of the Aβ plaques or in the compounds developed in the research for PET. Thus, the USPION maghemite was conjugated with Rhodamine or Congo Red, which were able to mark Aβ (1-40) fibrils in vitro. However, the in vivo use of Congo Red and its derivatives is not feasible due to its high toxicity and its inability to cross the BBB.

Zhou et al. and Zhang et al. (in Mater. Sci. Eng., 2014, C37, 348-355 and in Clin. Radiol., 2015, 70-74-80, respectively) were able to obtain NPs of the USPION type, linked to a carboxylic derivative of 1,1-dicyano-2-[6-(dimethylamino) naphthalene-2-yl]propene (DDNP), which was able to bind to Aβ plaques. These nanoparticles did not cross the BBB, but once mannitol was used, a loss of the T2 signal in the brains of transgenic mice in vivo was achieved. However, different authors (Nordberg et al., in Current Opinion in Neurology 2007, 20 (4): 398-402; Henriksen G. et al., in Eur J Nucl Med Mol Imaging, 2008, 35: S75-S81; Tolboom et al in J. Neurol Neurosurg Psychiatry 2010; 81: 882-884) have shown the low specificity of DDNP for the detection of amyloid plaques, so its use has been discarded.

Cheng et al. (in Biomaterials, 2015, 44 155e172) conjugated curcumin to the surface of magnetic iron NPs and stabilized them with the use of the block copolymer PEG-PLA and later, with PVP. It is stated that these conjugated NPs have a diameter below 100 nm and, according to Cheng, show low cytotoxicity and cross the BBB, both in the brain of AD transgenic mice (Tg-2576) and in non-transgenic mice. Ex vivo studies of MRI show more dark spots in the brain tissue of Tg mice than in control mice. Therefore, they raise the potential use of this CA for the early diagnosis of AD. However, the high lipophilicity of curcumin is recognized, which causes nonspecific recognition in the brain tissue when it binds to the white matter, and also its low ability to cross the BBB.

Kouyoumdjian et al. (in ACS Chem. Neurosci, 2013, 4, 575-584) used super-magnetic NPs of iron oxide conjugated with a ganglioside of the sialic acid type to obtain glyconanoparticles that, according to these authors, are related to amyloid plaques and allow their in vitro and ex vivo detection by MRI. However, the in vivo use of this macromolecule must affect the immune system of the brain so it is toxic.

On the other hand, it is known that in patients with neurodegeneration there is an increase in the presence of iron deposits in the brain, which could be an interesting biomarker for the diagnosis of AD, Parkinson's disease, multiple sclerosis and Huntington's disease. This approach has been addressed by Martinez-Lorca et al. (in Rev Neurol 2017; 64: 480), which describe the increased presence of iron and the protein that stores the iron—ferritin—in an area of the hippocampus of AD transgenic mice, specifically around the amyloid plaques. This finding has served as a basis for developing functionalized NPs with an antibody that recognizes ferritin. According to the authors, the accumulation of NPs in the indicated area produces a significant decrease in the T2 values in the MRI. A drawback of this method is that the ferritin protein also circulates in the plasma, where the iron is transported. It has been shown that ferritin in the plasma pass in the cerebral parenchyma through the BBB, using the ferritin-H receptor present in the membrane. Therefore, the plasma ferritin could saturate all the antibody recognition sites available in the iron oxide nanoparticles, thus avoiding the binding of the nanoconjugate to the ferritin present in the brain parenchyma. Future work will be necessary to increase the bonding capacity and affinity of the nanoconjugate. Another limitation of the method that employs these conjugated nanoparticles is that they require the use of mannitol to permeabilize the BBB.

The synthesis and preparation of metallic NPs constitutes one of the biggest challenges for the inclusion of nanotechnology in medical practice, mainly due to the requirements of the final product.

Ferrimagnetic iron oxide NPs ($Fe_3O_4$ and $\gamma$-$Fe_2O_3$) can be synthesized by several methods, both in liquid phase: coprecipitation (Lu et al. in Angewandte Chemie International Edition, 2007, 46 (8): 1222-1244), hydrothermal synthesis (Zheng et al., in Materials Research Bulletin, 2006. 41 (3): 525-529), decomposition in organic medium (Hyeon et al., in Journal of the American Chemical Society, 2001, 123 (51): 12798-12801) and microemulsions (Lawrence et al in Advanced Drug Delivery Reviews, 2012, 64: 175-193), as in gas phase: aerosol pyrolysis and laser pyrolysis (Bautista et al., in Journal of Magnetism and Magnetic Materials, 2005, 293 (1): p. 20-27).

In the case of the synthesis of Gd oxide NPs, the reported methods are: polyol, hydrothermal, sol-gel, template assisted technique, laser ablation, electron beam evaporation and mechanochemical (Gayathri et al. Bionanoscience 2015, 9 (6), 409-423).

In general, the most used organic coatings for obtaining stable NPs are: polyethylene glycol (PEG) (Faucher et al in ACS Applied Materials & Interfaces 2012, 4 (9), 4506-4515), polyglycolic acid or polylactic acid (PLGA), dendrimers, chitosan (Liu et al in Biomaterials 2012, 33 (21), 5363-5375, Tokumitsu et al in Chemical and Pharmaceutical Bulletin 1999, 47 (6), 838-842), sodium alginate and dextran (McDonald et al., in Academic Radiology 2006, 13 (4), 421-427). They have the advantage of being able to be incorporated to the NP surface in situ in the same synthesis process. In addition, they have numerous functional groups that allow interaction with the metallic core and are characterized by having great biocompatibility.

SUMMARY OF THE INVENTION

The new nanoparticles, coated, functionalized and conjugated with the naphthalene derivatives, have general Formula I;

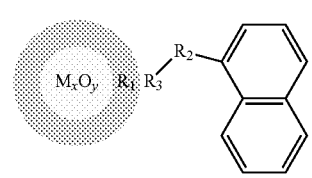

Formula I wherein:
- $R_1$: is an organic coating to the metal oxide core, of polymeric type, catechol derivatives and trialkoxyalkylaminosilane;
- $R_2$: —NHCO-alkylenyl-C(O)NH-alkylenyl-$R_3$;
- $R_3$: —COO—, —CO—, —NH, —O—, —S—, —NH-alkylenyl-NH—, —$NR_4$—CSS—;
- $R_4$: —H, —$CH_3$, —$CH_2$—$CH_3$, —$CH_2CH_2CH_3$, and
- $M_xO_y$: iron oxide ($Fe_3O_4$/$\gamma Fe_2O_3$), gadolinium oxide (III), manganese oxide(II) and copper(II) oxide;

wherein the conjugated, functionalized and coated magnetic nanoparticle is capable of, when it is administered to a mammal, crossing the blood-brain barrier and specifically binding to the agglomerates and amyloid plaques present in brain tissue;

wherein with this nanoparticle bound to the agglomerates and β-amyloid plaques in the brain tissue, hypo- or hyper-intense signals are observed in the region of interest through MRI.

The compounds of Formula I are capable of acting as positive (T1) and/or negative (T2) contrast agents for MRI for the early and non-invasive diagnosis of AD, through a hypo- or hyper-intense signal of the β-amyloid agglomerates or Aβ plaques.

In the NPs of Formula I, the metallic oxide magnetic core is coated with a functionalized polymeric layer that allows conjugation to naphthalene compounds, the preparation of which has been previously described in CU 2010/0204, EP 2 436 666 A20, P58243ZA00, U.S. Pat. No. 9,764,047, CA 2789869C, PI 2012003534.

The covalent and stable bond between the two chemical units form, in the NPs, a carbon chain with a singular structure, which surprisingly facilitates the NPs passage through the BBB, without the use of a disrupting agent, what are not described in the current state-of-the-art.

These NPs unexpectedly enhance the affinity and selectivity properties of the naphthalene derivatives towards the Aβ agglomerates and β-plaques, they are stable molecules and do not show toxicity. We are not aware that the compounds presented in this invention have been previously reported.

BRIEF DESCRIPTION OF THE DRAWINGS

FIGS. 4A-B: TEM micrographs of the NPs-1A, registered in a JEM-1010 electronic microscope, JEOL at 80 kV are presented.

FIG. 13 A—shows the longitudinal relaxation curves; with a fixed Echo Time (TE=11 ms) and different values of TR, while FIG. 13 B—shows the transversal relaxation curves, with a Fixed Repetition Time (TR=10000 ms) and different TE values. C—Comparative study of relaxivities of Resovist and NPs-1A by MRI.

FIG. 14A shows the longitudinal relaxation curves; with an Echo Time (TE=11 ms) fixed and different values of TR, while FIG. 14B shows the transversal relaxation curves, with a Fixed Repetition Time (TR=10000 ms) and different TE values.

DETAILED DESCRIPTION

Figure 1A:
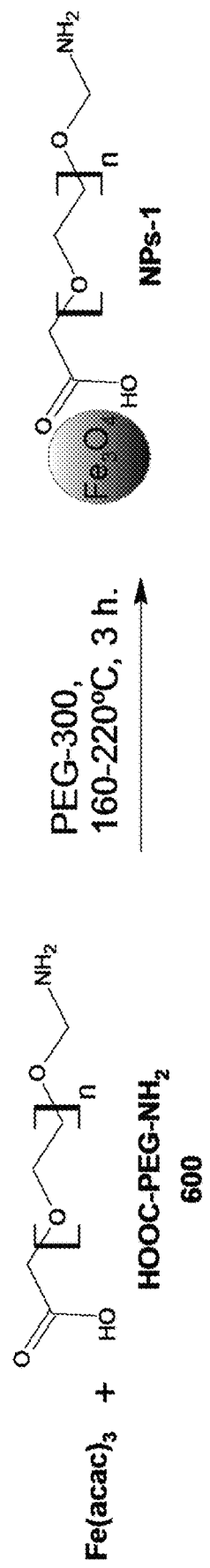
FIGS. 1A-B: show the general procedure, which includes the most significant reaction conditions, of the conjugation of NPs-1 magnetite nanoparticles functionalized with HOOC-PEG-$NH_2$ and conjugated with N-[4-(1-naphthylamino)-4-oxobutanoyl]-β-alanine (A) to obtain NPs-1A.

This invention is related to Chemistry and Physics applied to the field of Medicine and refers to the use of compounds with magnetic properties, which belong to the category of metal oxide nanoparticles, coated and conveniently functionalized, which are conjugated with naphthalene compounds related to agglomerates and β-amyloid plaques present in neurodegenerative diseases. These new nanoparticles (NPs) are used for the non-invasive detection of agglomerates and amyloid plaques using the Magnetic Resonance Imaging (MRI) technique. The nanoparticles described here cross the blood-brain barrier (BBB), without the use of any membrane-disrupting agent. Likewise, they bind with high affinity and specificity to the agglomerates and β-amyloid plaques, and are used as contrast agents in MRI for the early detection of Alzheimer's disease (AD).

The present invention relates to the use of metal oxide nanoparticles with magnetic properties, coated, functionalized and conjugated to naphthalene compounds highly related to agglomerates and β-amyloid plaques. The design of the NPs presented here was based on the analysis of the structure of the senile plaques, specifically the agglomerates of the Aβ peptide, to avoid nonspecific recognition with other brain structures. To do this, different databases and computer programs were analyzed in a combined and singular way (3D structure of fibrils Aβ 1-42 of Alzheimer's, Code: 2BEG, DOI: 10.2210/pdb2beg/pdb, deposited: 2005 Oct. 24, published: 2005 Nov. 22, Wyrzykowska et al Nanotechnology 2016, 27 445702; Chen, et al., in J. Mol. Biol. 2005; 354: 760-776; Landau et al., in PLoS Biol. 2011; 9: e1001080, Hetényi et al in Biochem Biophys, Res. Commun 2002; 292: 931-936) and it was obtained that the NPs described here interact unexpectedly with the Aβ peptide, mainly with amino acid residues, essentially through interactions hydrophobic, Van der Waals forces and H-bonds. Thus, the estimated energy values ΔG (−9.8 to −6.6 kcal/mol) and the affinity constant Ki (1.33×10$^{-7}$ to 2.79×10$^{-7}$) of the β-amyloid peptide-organic coating complex of NPs, demonstrate the stability of these NPs with plaques. Accordingly, the NPs interact with the Aβ peptide in the region that appears to be key in the formation of the β-folding structure (Chen et al., in the Journal of Molecular Biology, 2005, 354 (4): 760-776; Hetényi et al in Biochemical and Biophysical Research Communications 2002, 292 (4): 931-936). The design of these functionalized NPs includes a carbon chain that carries different functional groups that allow the selective conjugation with the naphthalene derivatives, giving rise to a new chain that responds structurally with the synergy of both structures, and that also, surprisingly, it helps NPs claimed in this patent cross the BBB, solving the drawbacks encountered with other CA in the prior state-of-the-art and overcoming the described technique.

The present invention entails the use of new functionalized and conjugated magnetic nanoparticles to diagnose Alzheimer's disease in early stages by Magnetic Resonance Imaging. These nanoparticles of Formula I comprise a metal oxide core coated with a multifunctional organic layer, wherein said organic layer is conjugated to a naphthalene derivative related to the β-amyloid plaques,

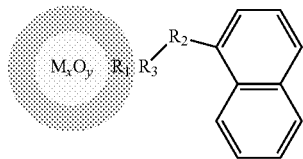

Formula I wherein:
$R_1$: is an organic coating to the metal oxide core, of polymeric type, catechol derivatives and trialkoxyalkylaminosilane;
$R_2$: —NHCO-alkylenyl-C(O)NH-alkylenyl-$R_3$;
$R_3$: —COO—, —CO—, —NH, —O—, —S—, —NH-alkylenyl-NH—, —$NR_4$—CSS—;
$R_4$: —H, —$CH_3$, —$CH_2$—$CH_3$, —$CH_2CH_2CH_3$, and
$M_xO_y$: iron oxide ($Fe_3O_4$/γ$Fe_2O_3$), gadolinium oxide (III), manganese oxide (II) and copper (II) oxide;
wherein the coated, functionalized and conjugated magnetic nanoparticle is capable, when administered to a mammal, of crossing the blood-brain barrier and specifically binding to the agglomerates and amyloid plaques present in brain tissue;
wherein, with the nanoparticle bound to the agglomerates and amyloid plaques in the brain tissue, hypo- or hyper-intense signals are observed in the region of interest through magnetic resonance imaging.

Through the NPs described here, the acquisition of Magnetic Resonance Imaging is carried out to detect the agglomerates and β-amyloid plaques present in the brain. These NPs cross the BBB, without the use of any membrane disrupting agent, due to the synergy of properties that arise from the combination of the use of specific coatings for each naphthalene derivative related to the β-amyloid plaques.

Unexpectedly, without being bound by theory, the singular combination of the naphthalene derivatives, related to the β-amyloid plaques, with the coatings used, allows the obtaining of CA of the type T1 and T2, by varying only the metal oxide core, which guarantees a greater precision in the diagnosis. In the state-of-the-art this property is not reported for the same compound.

The NPs of this invention can be used at low concentrations because they are highly related to β-amyloid agglomerates and their values of relaxitivities modify the contrast by more than 40%, which guarantees a high sensitivity.

In this invention, the general methods of synthesis of the new functionalized nanoparticles of metal oxides with magnetic properties, conjugated to the aforementioned naphthalene derivatives, with good yields, and their use for the diagnosis of Alzheimer's Disease are described, which should not be construed as limiting the present invention in any way. The procedures are practical, economical and can be adapted to a larger scale manufacturing.

Figure 1B:
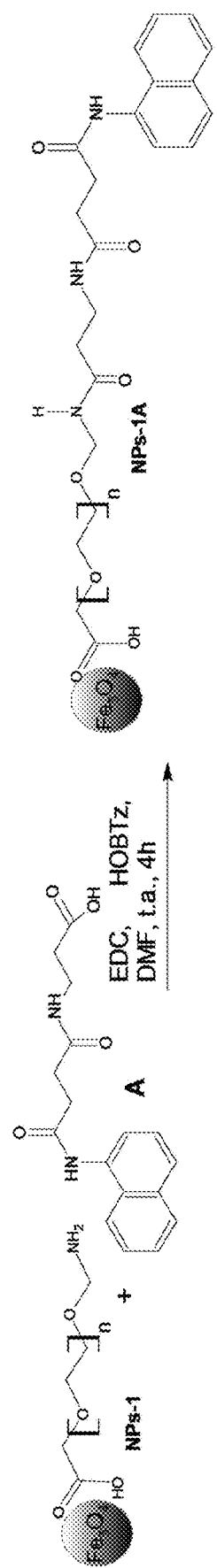

A non-limiting example of the magnetic, and highly monodisperse synthesized NPs were NPs of iron oxide ($Fe_3O_4$/γ$Fe_2O_3$) coated with polyethylene glycol functionalized with carboxyl and amine groups. These coatings offer the advantage of forming an amide bond with an amino or carboxyl group, respectively, of a naphthalene derivative, related to the agglomerates and 3-amyloid plaques, such as, for example, the acids: N-[4-(1-naphthylamino)-4-oxobutanoyl]-β-alanine (A) or 6-{[4-(1-naphthylamino)-4-oxobutanoyl]amino}hexanoic acid and the amines: N1-(2-aminoethyl)-N4-(1-naphthyl) succinamide (B) or N1-(4-aminobutyl)-N4-(1-naphthyl) succinamide, respectively. The formation of the covalent bond carried out through the method known as the Steglich reaction or the carbodiimide method (Xia et al., in Int. J. Electrochem, Sci, 2013. 8: 2459-2467). In Example 2, which is not limiting to the patent, magnetic NPs functionalized with N-[4-(1-naphthylamino)-4-oxobutanoyl]-β-alanine (NPs-1A) were synthesized according to the scheme shown in FIGS. 1A-B, which is not limiting. Subsequently they were isolated, washed, and dispersed in DMSO, at room temperature.

Figure 2:
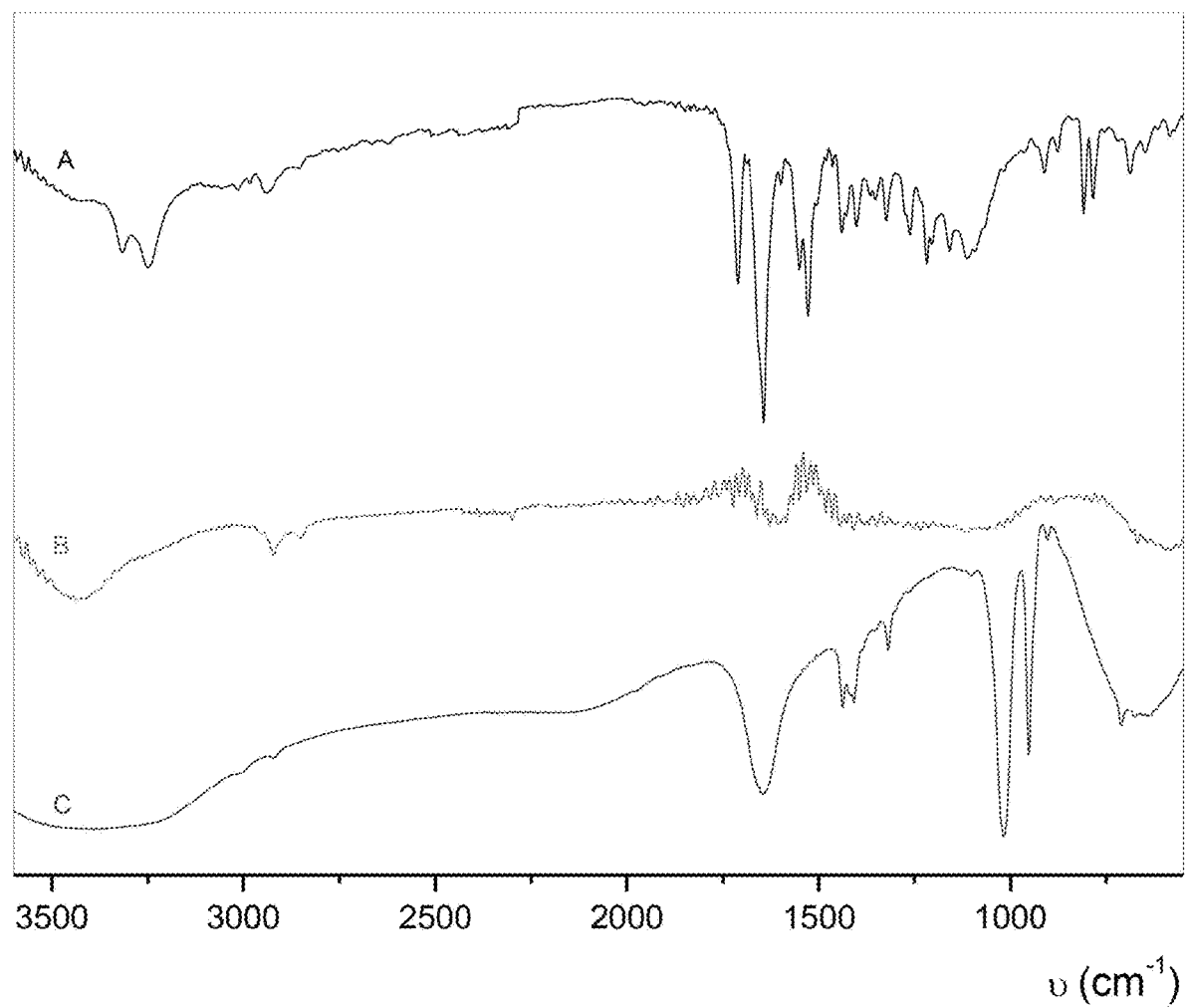
FIG. 2: shows the FT-IR spectra of A: N-4-(1-naphthylamino)-4-oxobutanoyl-β-alanine (A), B: NPs-1 and C: NPs-1A.

The structural characterization of NPs-1A was carried out using different analytical techniques. FIG. 2 shows the FT-IR spectra of the synthesized NPs, of N-[4-(1-naphthylamino)-4-oxobutanoyl]-β-alanine and NPs-1A, where the presence of N-[4-(1-naphthylamino)-4-oxobutanoyl-β-alanine (A) on the surface of the NPs synthesized is demonstrated.

In the FT-IR spectrum of the NPs-1 appears the set of typical bands of this type of system. Thus, at 3420 cm$^{-1}$, a band appears corresponding to the valence vibration of the —NH$_2$ group. At 2920 and 2850 cm$^{-1}$ the valence vibrations $v^{as}_{(CH)}$ and $v^{s}_{(CH)}$ of the carbon chain of the PEG are observed. Finally, at 580 cm$^{-1}$, the characteristic band of $v_{(Fe—O)}$ appears confirming the presence of magnetite in the NPs.

On the other hand, in the FT-IR spectrum of the NPs-1A, the signals that corroborate the coupling of the terminal carboxyl group of N-[4-(1-naphthylamino)-4-oxobutanoyl-β-alanine (A) with the terminal amino group of NPs-1 is observed. Thus, the valence vibration bands $v_{(OH)}$ and $v_{(CO)}$ of N-[4-(1-naphthylamino)-4-oxobutanoyl-β-alanine (A), at 3248 cm$^{-1}$ and at 1711 cm$^{-1}$, respectively, disappear. This confirms that the free carboxyl group of the naphthalene derivative (A) reacts, giving rise to an amide bond, whose vibration band is observed at 1645 cm$^{-1}$. There also appear, a broad band at 3370 cm$^{-1}$ and another intense at 1018 cm$^{-1}$, which are attributed to $v_{(NH)}$ and to $v_{(C—O—C)}$, respectively. The valence vibration band $v_{(Fe—O)}$ is observed at 640 cm$^{-1}$.

In Table 1 it is reported that the iron content in the NPs-1A, determined by Atomic Absorption, ranges between 30-45%.

TABLE 1

| Sample | $M_{T\,NPs\text{-}1A}$ (mg) | $C_{NPs\text{-}1A}$ (mg/L) | $C_{Fe}$ (mg/L) | $M_{T\,Fe}$ (mg) | % Fe |
|---|---|---|---|---|---|
| 1 | 12.1 | 3 | 1.65 | 4.95 | 40.9% |
| 2 | 15.7 | 3 | 1.57 | 4.71 | 30.0% |
| 3 | 9.5 | 3 | 1.44 | 4.32 | 45.4% |

$$A = m*C_{Fe} + n$$

| Parameter | Value | Error | Error (%) |
|---|---|---|---|
| n | −0.0080 | 0.0004 | 5.0 |
| m (L/mg) | 0.0341 | 0.0009 | 2.6 |

Figure 3:
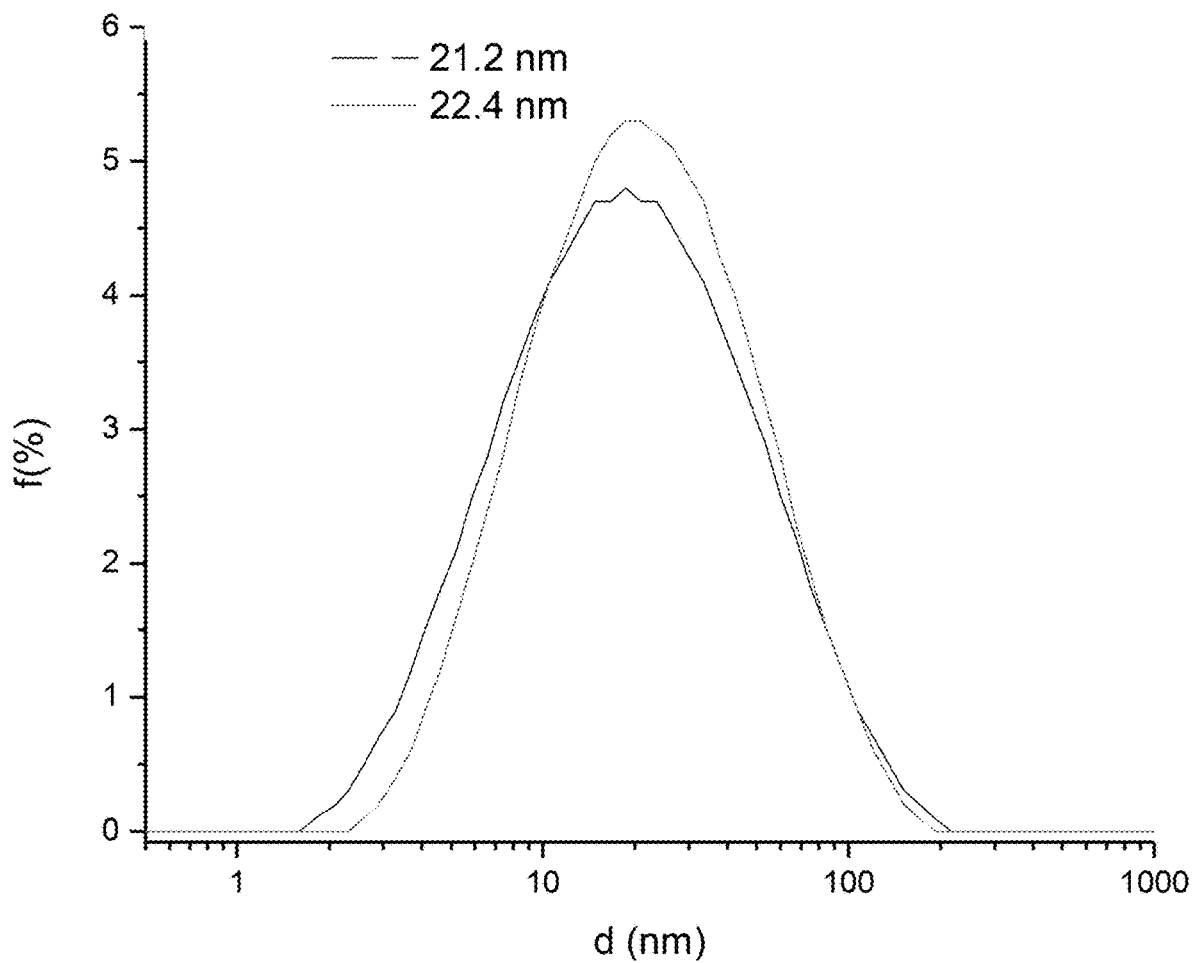
FIG. 3: shows the hydrodynamic diameter of the NPs-1A, dispersed in DMSO, determined by the DLS technique. Time between measurements 2 min. The DLS profiles were obtained in a DelsaNano C spectrometer from the Beckman Coulter firm. The measurements were made at an angle of 179°.
Figure 4A:
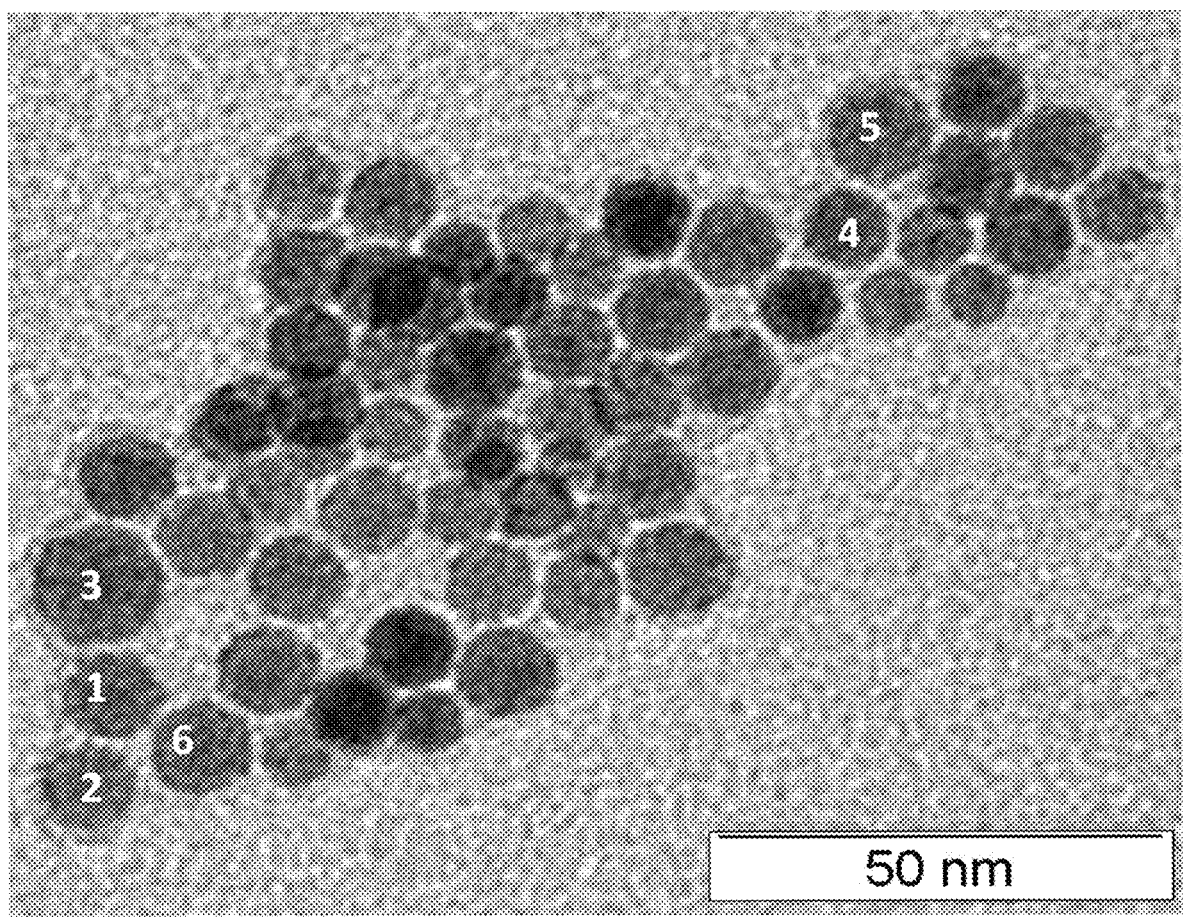

The measurement of the hydrodynamic diameter (DLS profile) of the NPs-1A was made with a time interval of two minutes (FIG. 3). The value of this parameter was around 21 nm, with a polydispersity index of less than 5%. In addition, the value of the diameter remained stable at the time of measurement, which shows that no agglomerates are formed in the system. This is due to the fact that N-[4-(1-naphthylamino)-4-oxobutanoyl-β-alanine (A), which has a special amidoalkyl chain, unexpectedly gives a high stabilization to NPs due to steric hindrance, without interactions between nearby particles. According to the TEM micrographs (FIG. 4A), the diameter of the NPs-1A is 11.1±1.8 nm (FIG. 4B). In them it is not possible to appreciate the organic coating on the surface of NPs-1A.

Figure 5A:
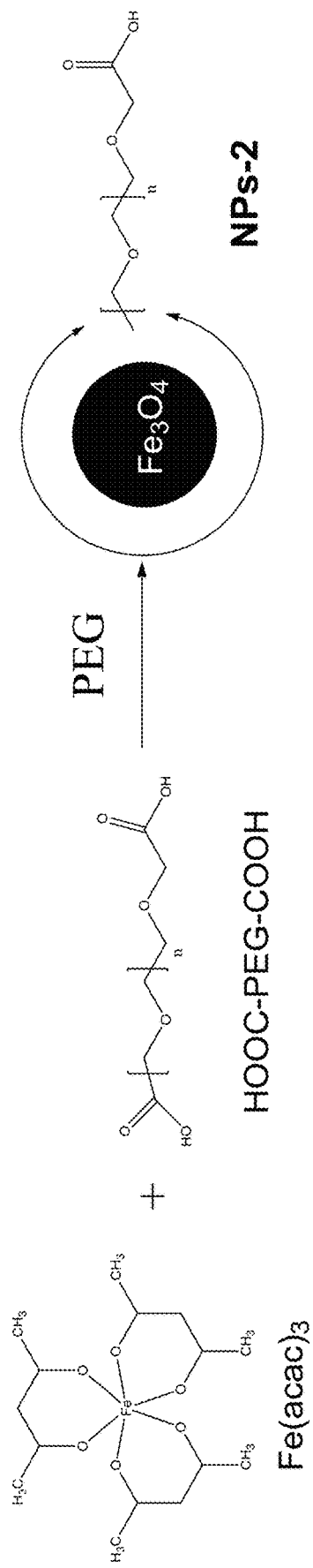
FIGS. 5A-C: show the general procedure, which includes the most significant reaction conditions, of the conjugation of magnetite nanoparticles NPs-2, functionalized with PEG-dicarboxylated, with $N^1$-(2-aminoethyl)-$N^4$-(1-naphthyl) succinamide (B) to obtain NPs-2B.
Figure 5B:
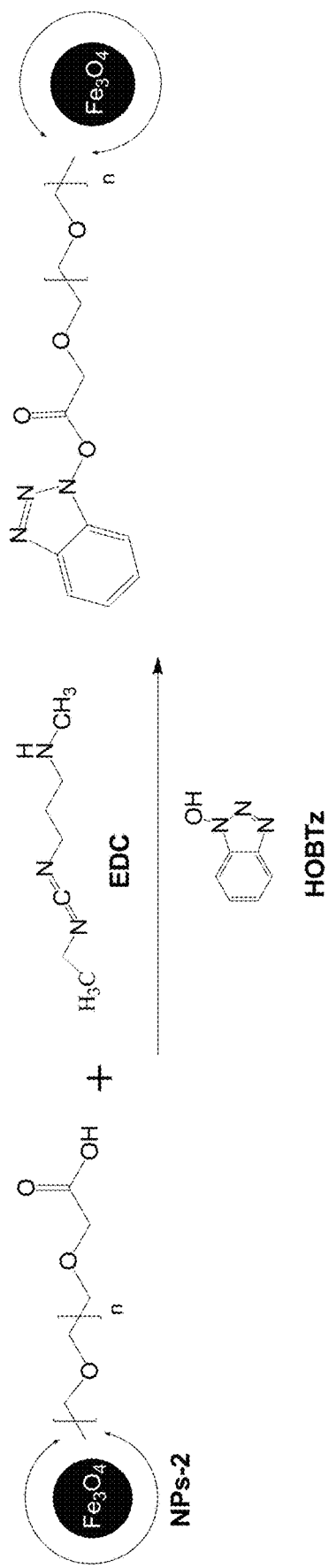
Figure 5C:
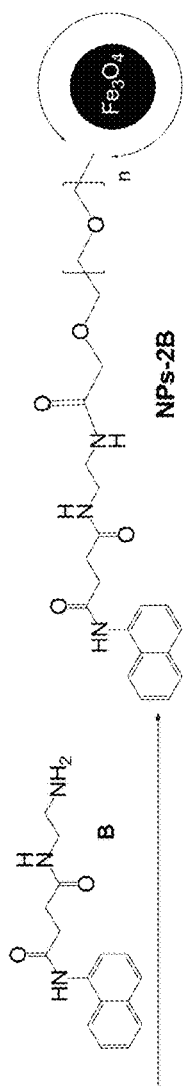
Figure 5C:
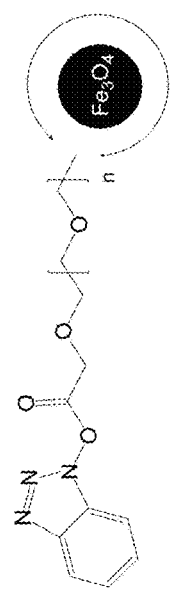
Figure 6:
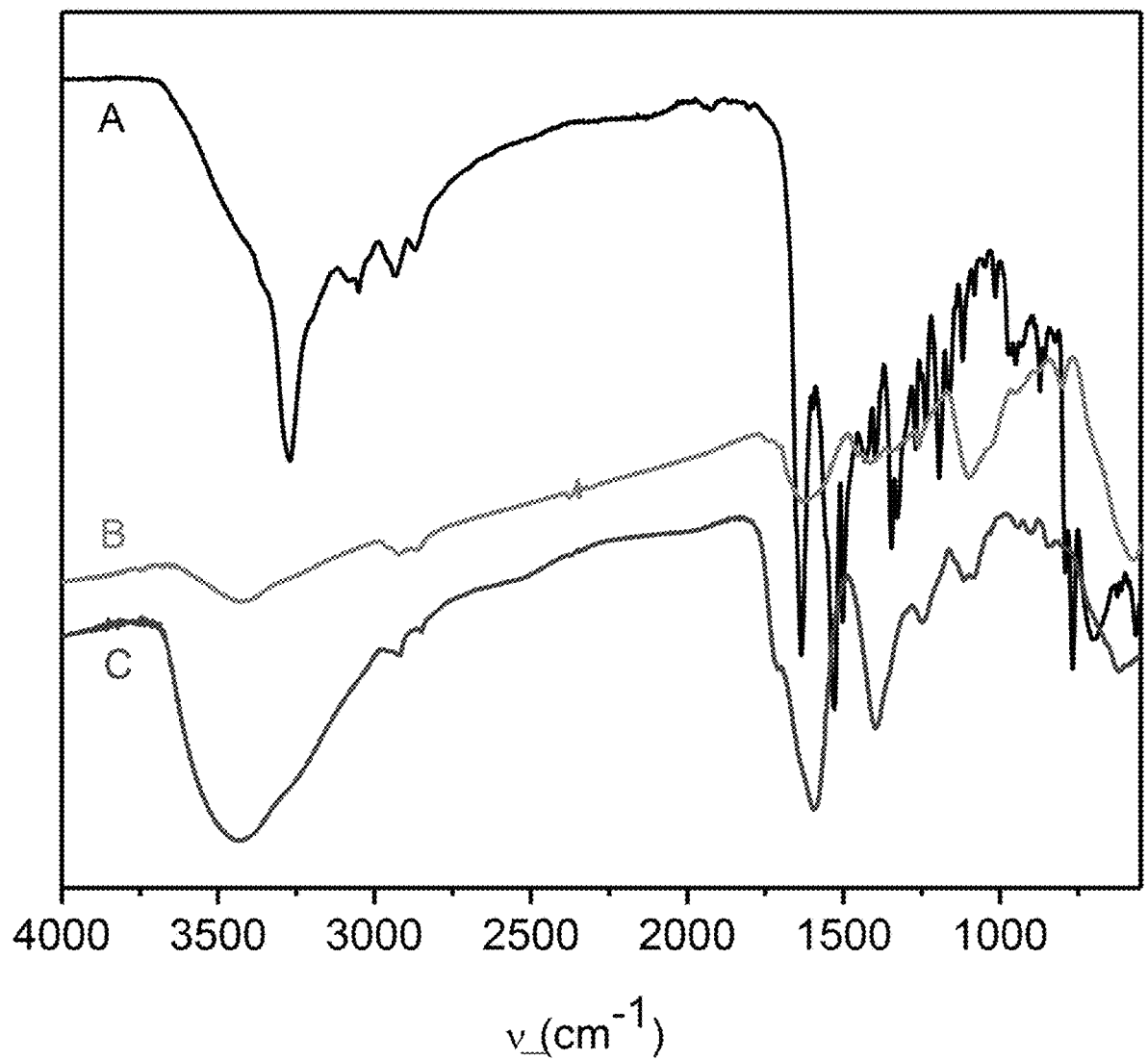
FIG. 6: shows the FT-IR spectra of A: $N^1$-(2-aminoethyl)-$N^4$-(1-naphthyl) succinamide (B), B: NPs-2 and C: NPs-2B.

The general procedure for the conjugation of N1-(2-aminoethyl)-N4-(1-naphthyl) succinamide (B) with the magnetite NPs coated with dicarboxylated PEG (NPs-2), is presented in FIGS. 5A-C, which is not limiting of this patent. The NPs-2B were separated magnetically and washed with DMF and subsequently with water to remove the residues from the reaction. Once the product was vacuum dried, the NPs were dispersed in DMSO and stored at room temperature until use. The chemical structure of NPs-2B could be verified through its FT-IR spectrum (FIG. 6).

In the spectrum of the NPs-2B a broad and intense band around 3432 cm$^{-1}$ is observed, which corresponds to the $v_{(NH)}$ in the secondary amides. Three bands are observed, at 1593 cm$^{-1}$ ($\sigma_{NH}$ and $v_{C=O}$) and at 1398 cm$^{-1}$ ($v_{CN}$), which show the presence of compound B in the structure, and also, at 616 cm$^{-1}$ the band of $v_{Fe\text{-}O}$ vibration.

Figure 7:
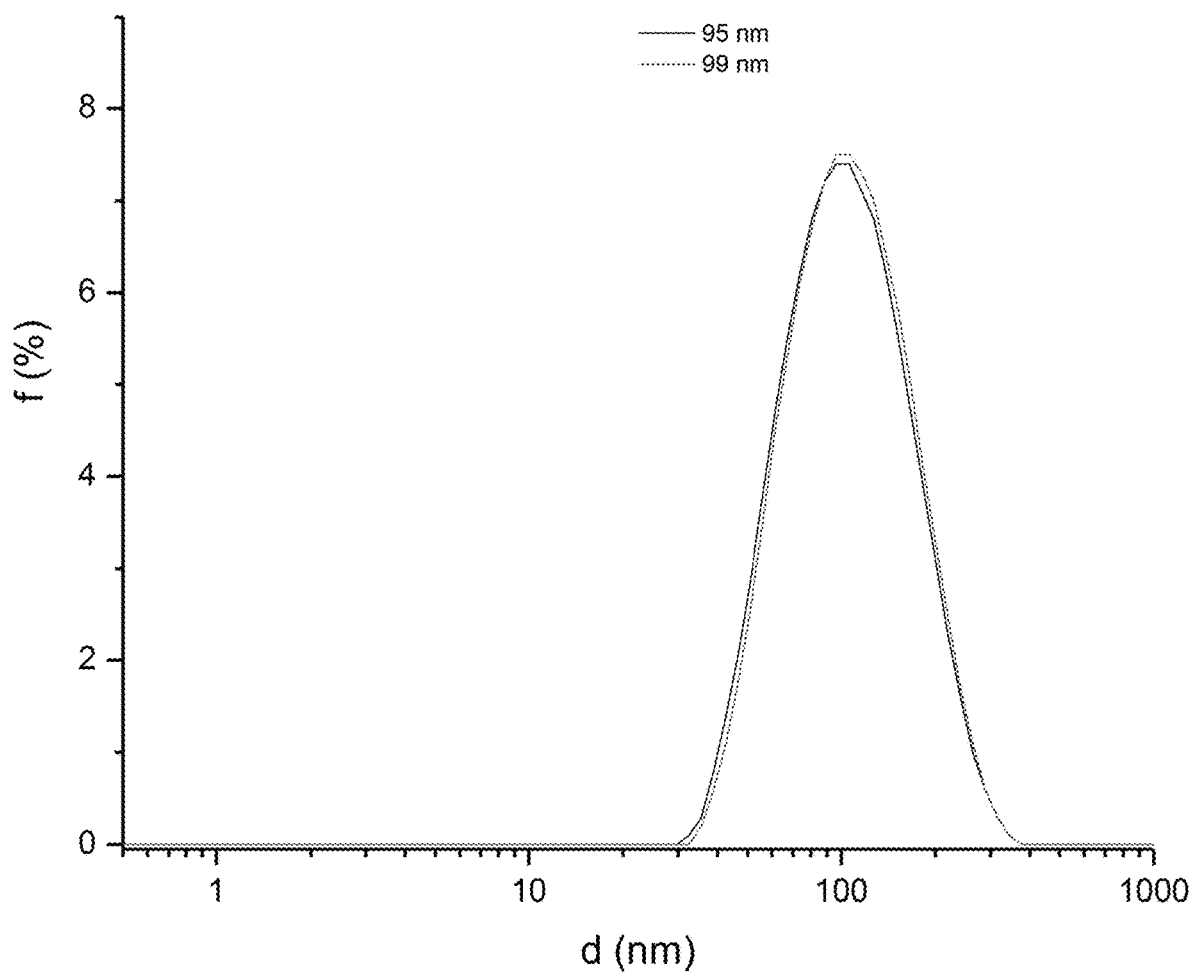
FIG. 7: shows the hydrodynamic diameter of the NPs-2B, dispersed in DMSO, determined by the DLS technique. Time between measurements 2 min. The DLS profiles were obtained in a DelsaNano C spectrometer from the Beckman Coulter firm. The measurements were made at an angle of 179°.

In FIG. 7, the DLS profiles of the NPs-2B are observed. The measurements made by DLS reported a hydrodynamic diameter of 95-99 nm with a polydispersity index of less than 16%. The stability of the NPs-2B was evaluated through measurements by DLS, at intervals of 2 minutes (FIG. 7). According to these results, there is no appreciable variation in the values of the hydrodynamic diameters of the NPs-2B, so the system favorably presents an adequate stability during the study time in DMSO. This is due to the conjugation of B with the NPs-2, which, as in the case of the NPs-1A, does not allow other molecular interactions to take place, so there is no tendency to agglomerate the NPs-conjugates. Therefore, it can be stated that the naphthalene derivatives, related to the agglomerates of β-amyloids, unexpectedly confers stability to the magnetic NPs of iron oxides.

Figure 8:
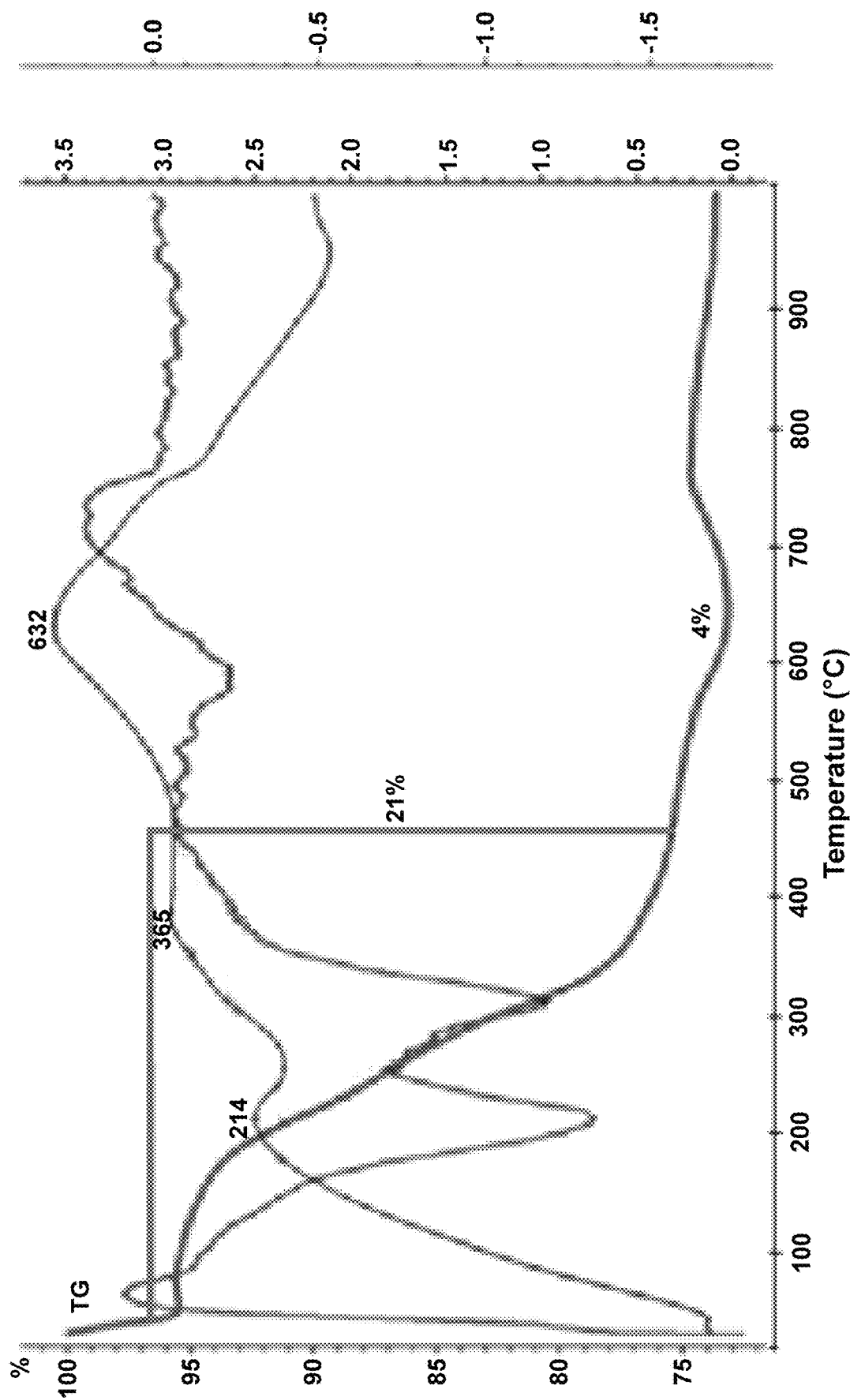
FIG. 8: shows the curves of thermograms (TG) and Differential Thermal Analysis (DTA) of the NPs-2B subjected to a thermal treatment from room temperature to 1000° C. under a flow of Ar. The simultaneous thermograms of ATD and TG were registered in a NETZSCH equipment, model STA 449 F3. The experimental data of the variation of the weight of the sample with the temperature were processed with the help of the program included in the equipment, "Proteus", version 5.2.1/07.04.2001. The error of the quantitative TG analysis is 2.0%.

FIG. 8 shows the thermograms corresponding to the thermogravimetric analysis (TG), the differential thermal analysis (DTA), as well as the thermogravimetric analysis (TGD) of the NPs-2B. The TG curve is characterized by the existence of a first stage of sudden loss of mass, which corresponds to the elimination of moisture from the sample. Then, a loss of 21% of the mass occurs from 125 to 460° C., with two maximums in the curve of ATD, at 214 and at 365° C.

This corresponds to an endothermic process of desorption and decomposition of the organic matter in the sample. A third loss of 4% of weight was recorded from 591° C., which is observed in the DTA curve as an endothermic process with a maximum at 632° C. Then, at 675° C., a weight gain occurs, which corresponds to a transition from the crystalline phase of magnetite to maghemite caused by oxidation. Finally, the hematite, the most stable thermodynamically crystalline phase, is obtained (Pati et al in J. Appl. Phys, 2012, 112: 210-220).

Figure 9A:
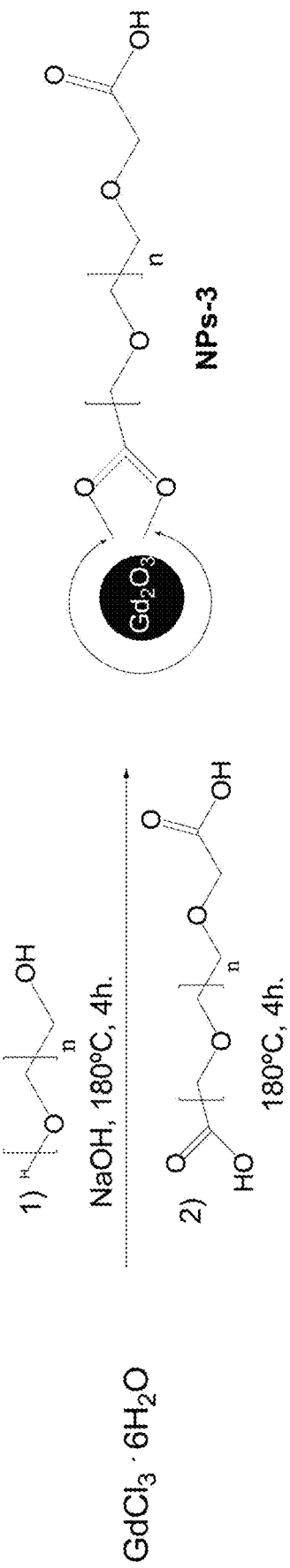
FIGS. 9A-C: show the general procedure, which includes the most significant reaction conditions, of the conjugation of gadolinium oxide nanoparticles functionalized with PEG-dicarboxylic (NPs-3), with N1-(2-aminoethyl)-N4-(1-naphthyl) succinamide (B) to obtain NPs-3B.
Figure 9B:
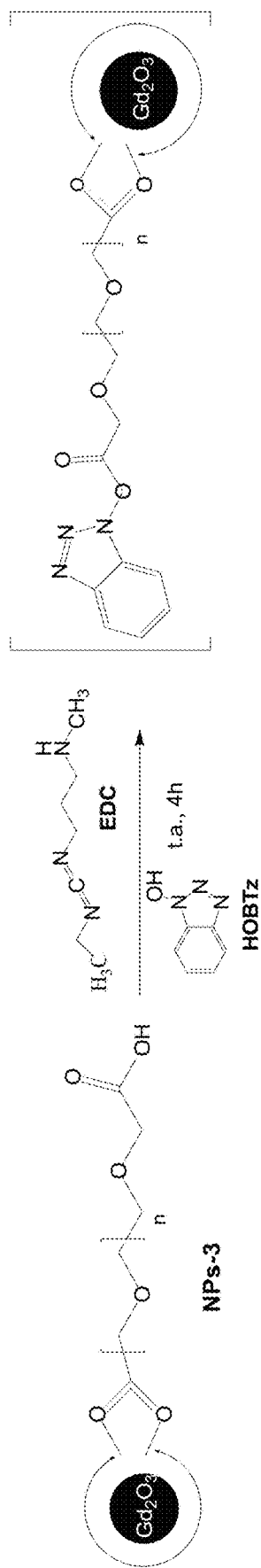
Figure 9C:
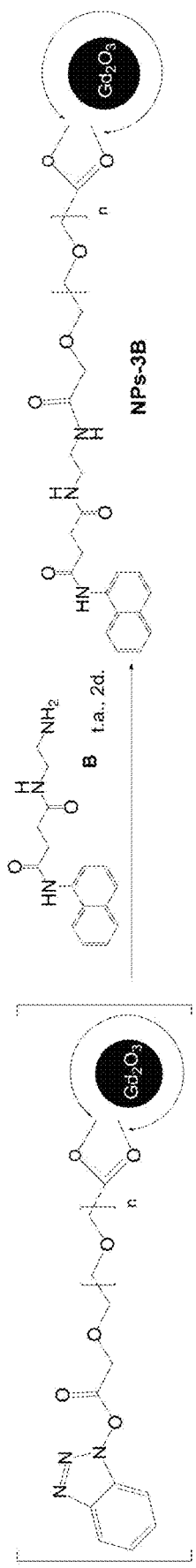

Another non-limiting example of the magnetic and highly monodisperse NPs claimed in this patent were the PEGylated Gd$_2$O$_3$ nanoparticles functionalized with naphthalene derivatives. These NPs can be coated with polyethylene glycol by the polyol method (Wasi Md. et al in Colloids and Surfaces A: Physicochemical and Engineering Aspects 2014, 450, 67-75). In FIGS. 9A-C, which is not limiting, the general synthesis procedure is shown, which consists of two stages. In the first stage, the nanoparticles coated with PEG are obtained and in the second stage, the ligands are exchanged with the dicarboxylated PEG (NPs-3). The conjugation of the NPs-3 with B is carried out by the Steglich reaction.

Figure 10:
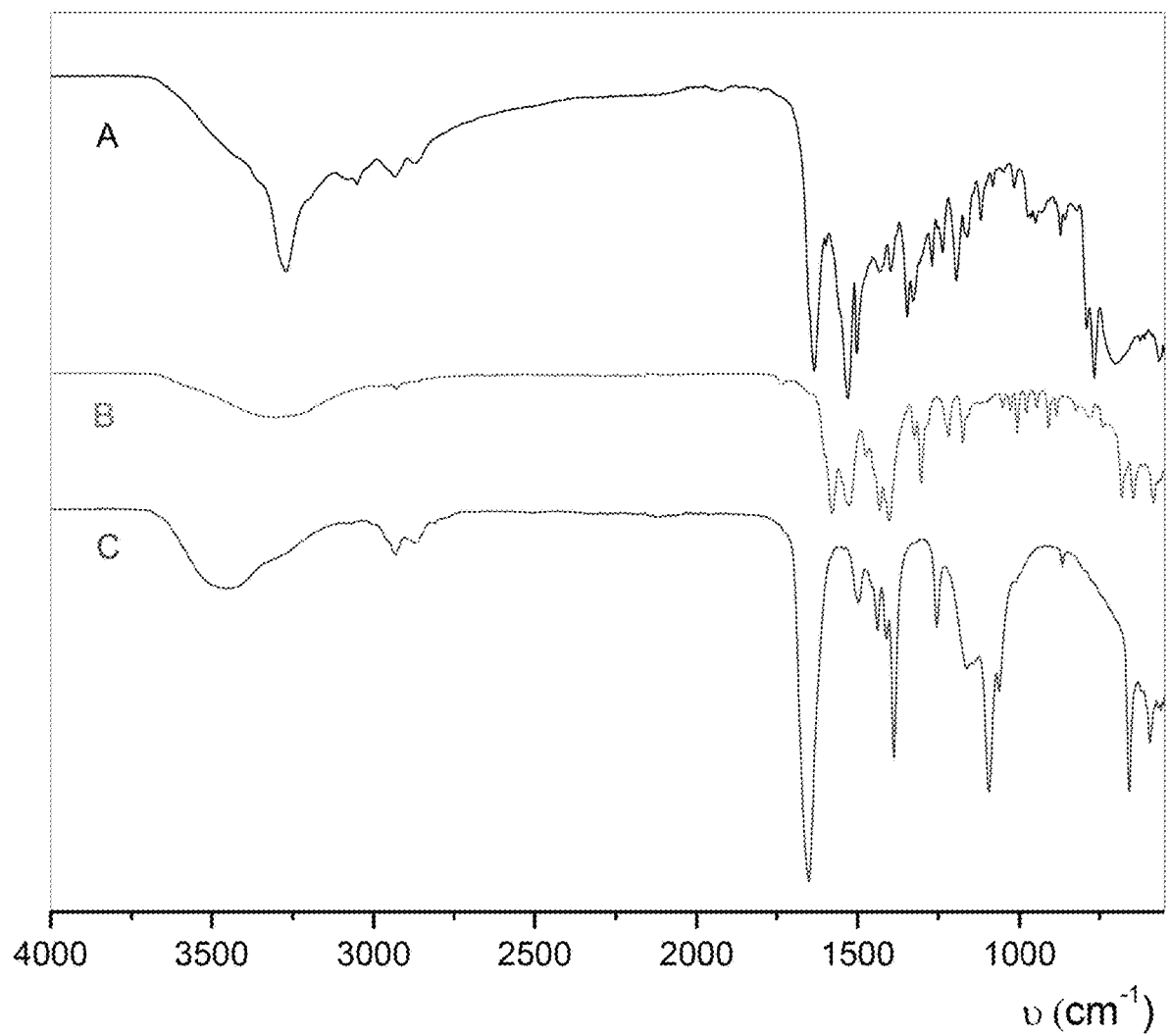
FIG. 10: shows the FT-IR spectra of A: N1-(2-aminoethyl)-N4-(1-naphthyl) succinamide (B), B: NPs-3 and C: NPs-3B.

In the FT-IR spectrum of the NPs-3B (FIG. 10), the presence of bands is observed at 1650, 1498 and 1387 cm$^{-1}$, which correspond to the vibrations of the antisymmetric valence ($v^{as}_{OCO}$) and symmetric ($v^{s}_{OCO}$) of the carboxylate of the dicarboxylated PEG linked to the Gd$_2$O$_3$, overlapped with those of the amide group that takes place ($\sigma_{NH}$, $v_{C=O}$ and $v_{CN}$). At 1387, 1255 and 1095 cm$^{-1}$, the bands characterizing the dicarboxylated PEG attached to the nanoparticles are observed. The broad band at 3454 cm$^{-1}$ is assigned to the valence vibration $v_{NH}$ of secondary amines.

The content of Gd in the NPs-3B was determined with the use of the optical emission spectrometry technique with inductively coupled plasma (ICP). The mean value obtained from two replicates was 30.29% (Table 2).

TABLE 2

| Replica | Concentration (ppm) | % mass |
|---|---|---|
| 1 | 6.118 | 30.59 |
| 2 | 5.997 | 29.99 |
| Lineal Equation | IE = 5153 × $C_{(Gd)}$ + 8408 | |
| Parameter | Value (ppm$^{-1}$) | standard error (ppm$^{-1}$) |
| Slope | 5153 | ±68 |
| Intercept | 8408 | ±314 |

The content of Gd was measured in an ICP-OES device, Spectro brand, Spectroflame model. The power used by the equipment was 1200 W. A nebulization flow of 1.2 L/min of Argon and a nebulization pressure of 3.8 bar was used. The auxiliary flow and the cooling flow were 1.2 L/min (Ar) and 18.8 L/min (Ar), respectively. The observation height was 15 mm with respect to the coil. $Gd_2O_3$ of 99.9% purity was used, which was dissolved in HCl (37%) to prepare the calibration curve.

Figure 11:
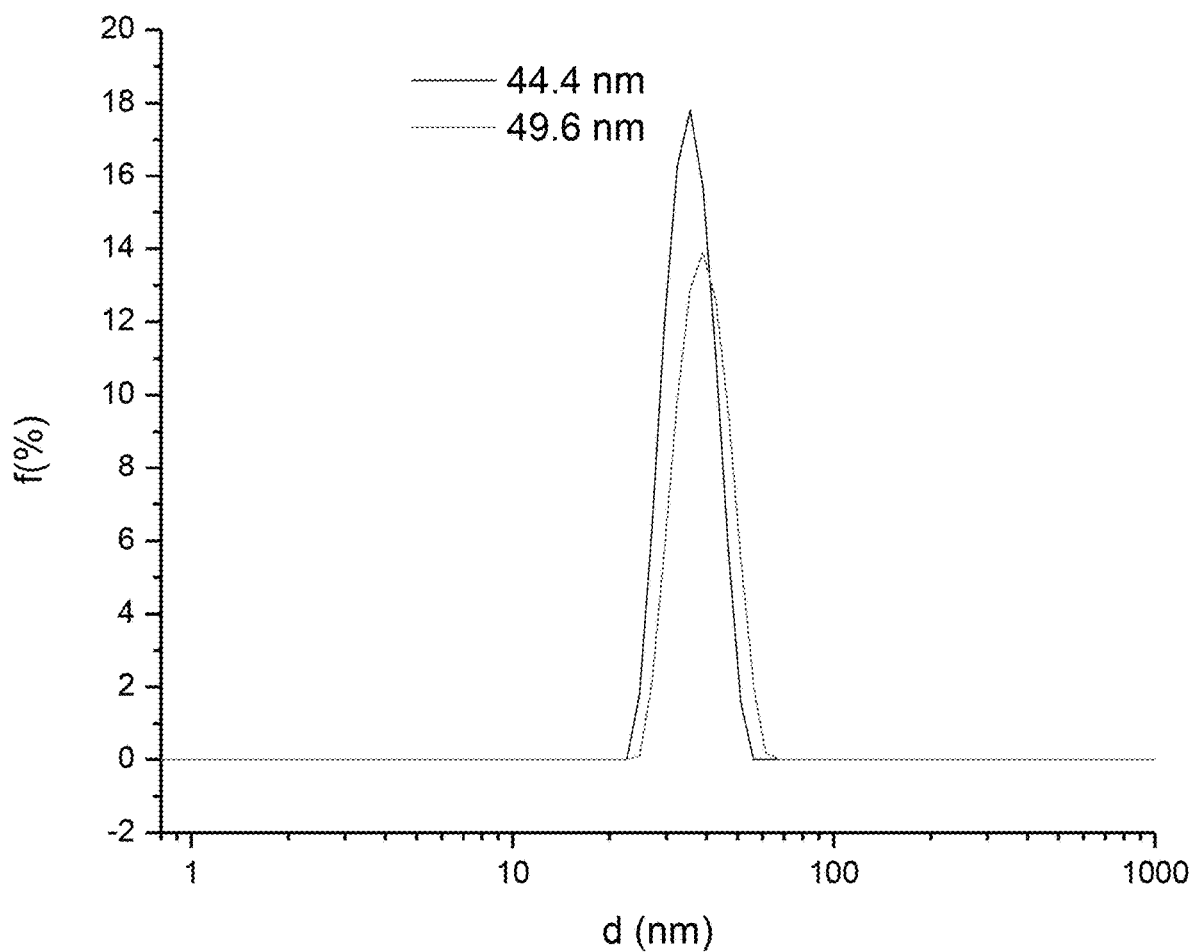
FIG. 11: shows the hydrodynamic diameters of the NPs-3B, dispersed in DMSO, determined by the DLS technique. Time between measurements 2 min. The DLS profiles were obtained in a DelsaNano C spectrometer from the Beckman Coulter firm. The measurements were made at an angle of 179°.

The hydrodynamic diameter of NPs-3B was determined through the DLS technique (FIG. 11). The hydrodynamic diameter was 47 nm, with a polydispersity index of less than 15%. Like the NPs-2B, the NPs-3B dispersed in DMSO maintained their stability over time.

Figure 12:
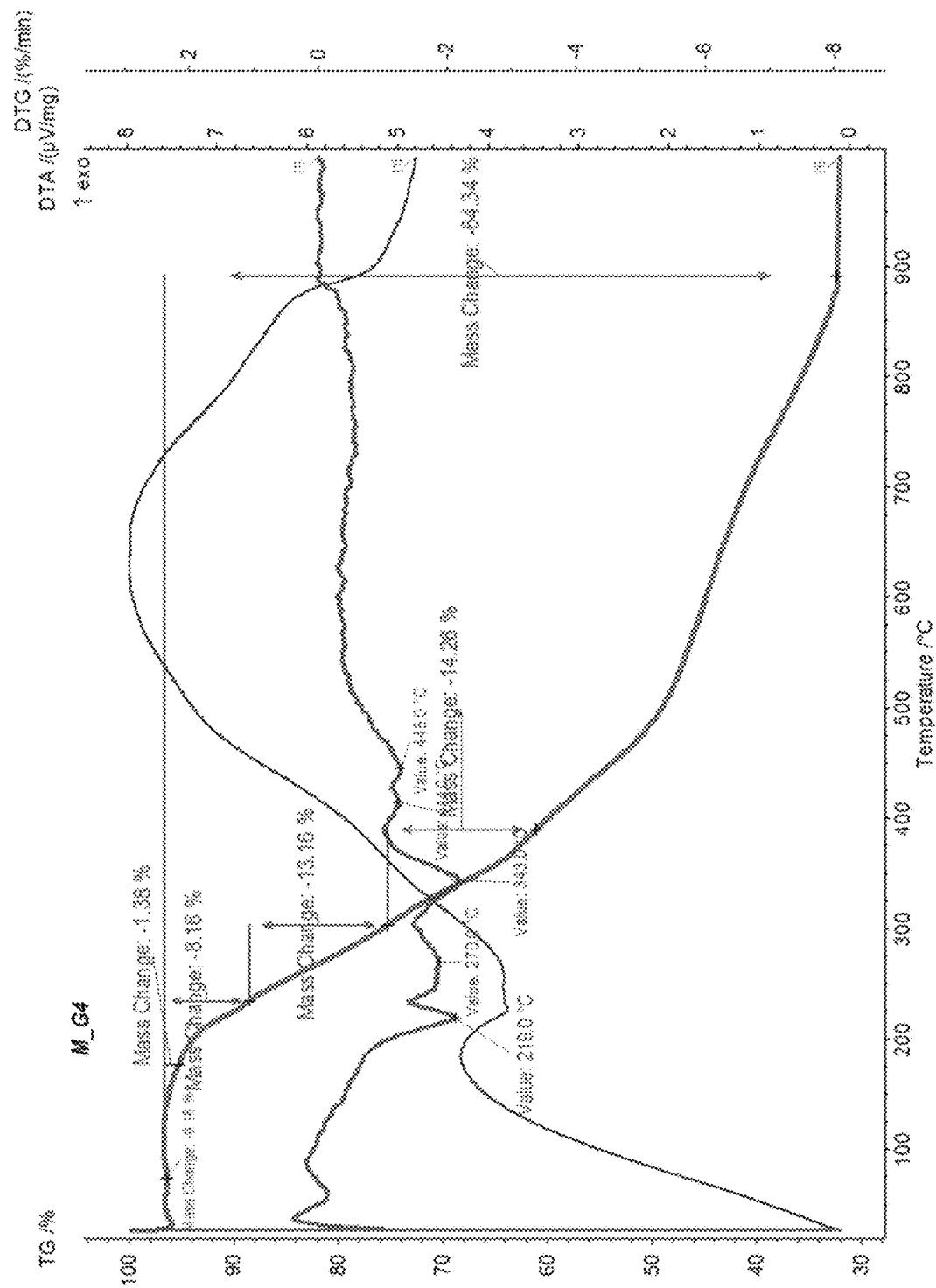
FIG. 12: the curves of thermograms (TG) and Differential Thermal Analysis (DTA) of NPs-3B subjected to a thermal treatment from room temperature to 1000° C. under an Ar flow are presented. The simultaneous thermograms of ATD and TG were registered in a NETZSCH equipment, model STA 449 F3. The experimental data of the variation of the weight of the sample with the temperature were processed with the help of the program included in the equipment, "Proteus", version 5.2.1/07.04.2001. The error of the quantitative TG analysis is 2.0%.

The thermal analysis provides information on the evolution of the sample against the temperature variation and allows to estimate the mass percentage of the surface coating of the Nps-3B. FIG. 12 shows the thermograms corresponding to the thermogravimetric analysis (TG), the differential thermal analysis (DTA), as well as the derivative of the thermogravimetric analysis (TGD). In the thermogram there is a small decrease in mass (0.18%) around 105° C., which is associated with the loss of hydration water in the NPs-3B. Then, and up to 900° C., a 64.34% loss of the total mass of the sample occurs, which is due to the processes of desorption and decomposition of the organic coating of the nanoparticles. As of 900° C., no significant changes in mass are observed, which corresponds to the nucleus of stable gadolinium oxide in the sample.

In order to measure the magnetic properties of the functionalized and conjugated NPs with the naphthalene derivatives of this invention, the relaxitivitie values of $r_1$ and $r_2$, and their relation $r_2/r_1$ (Example 7), were determined. This is a physical-chemical characteristic that reflects how the magnetic relaxation speed of a dissolution of a CA changes according to its concentration.

FIGS. 13 and 14 show the variations in the signal strength of the solutions of NPs-1A and NPs-3B prepared at different concentrations, as non-limiting examples. These curves are generated from measurements made in magnetic resonance imaging (MRI) obtained with Espin Eco sequences (Fanea L, et al. in Romanian Reports in Physics, 2011; 63 (2): 456-464).

Figure 13A:
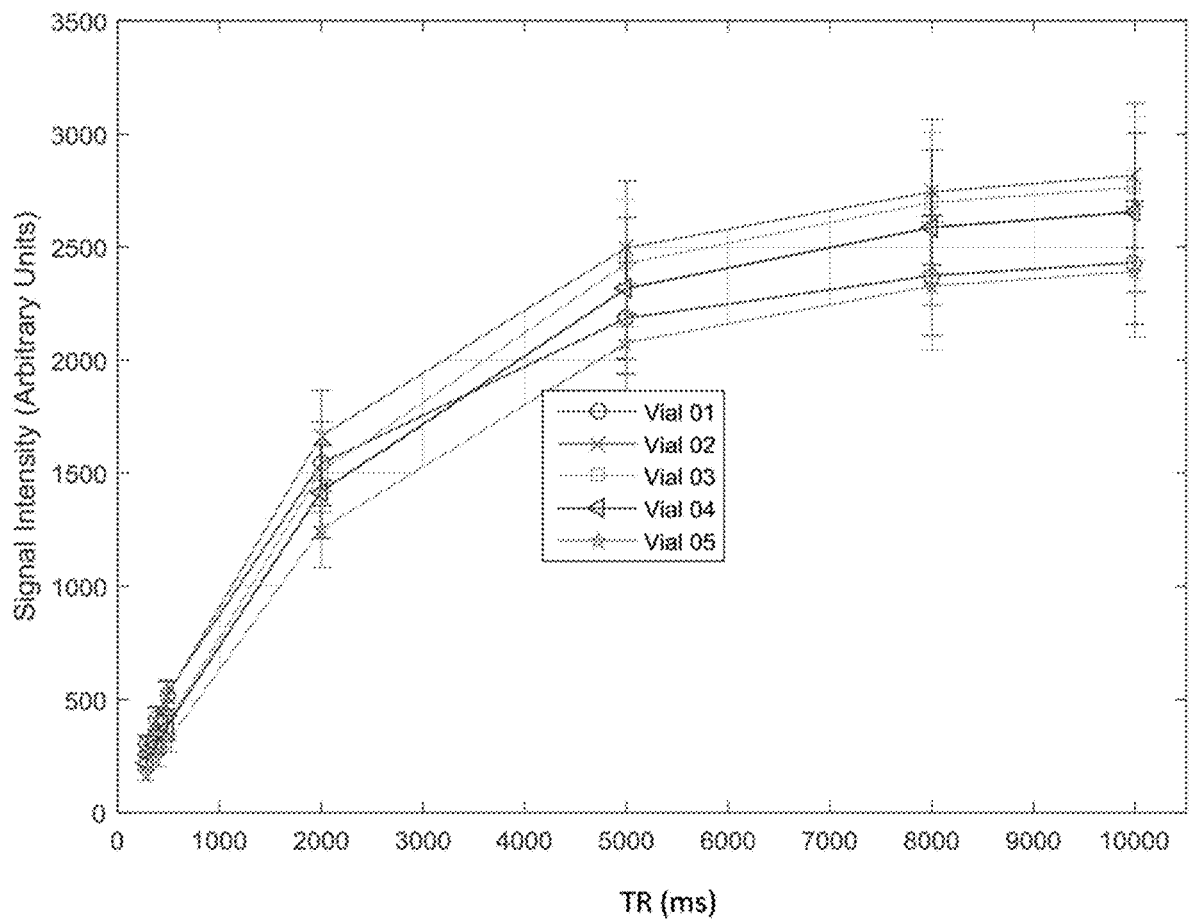
FIGS. 13A-B: shows the variations of the signal intensity of the NPs-1A prepared at different concentrations. These curves are generated from the measurements made in the magnetic resonance imaging (MRI) obtained with Spin Eco (SE) sequences.
Figure 13B:
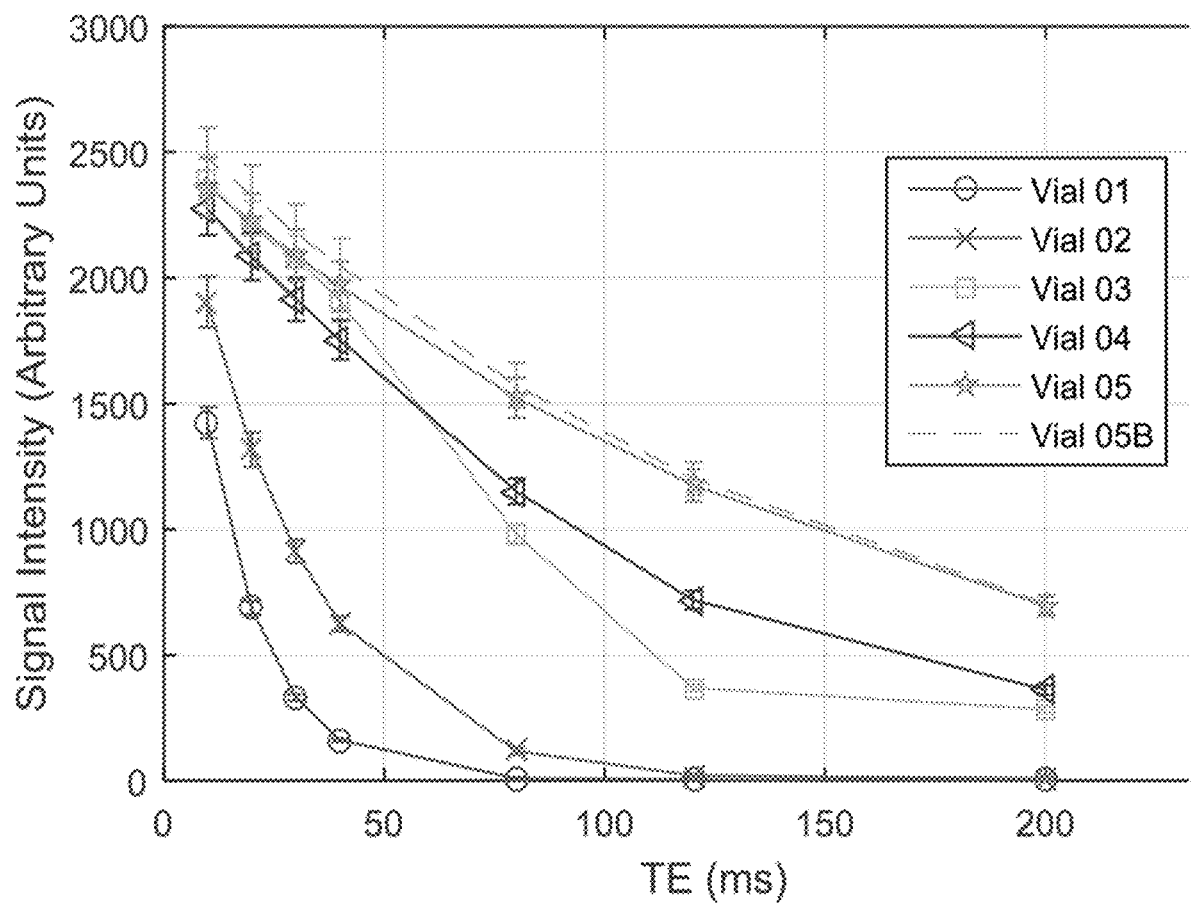

FIG. 13A shows the longitudinal relaxation curves for a fixed Echo Time (TE=11 ms) and different TR values, while FIG. 13B shows the transverse relaxation curves, with a Repetition Time (TR=10000 ms) fixed and different TE values. The ratio of relaxitivities $r_2/r_1$ evaluated from the experimental data was $r_2/r_1$=90, for the MRI equipment of 3T (Table 2.5).

TABLE 2

| Parameters | NPs-1A | Resovist* |
|---|---|---|
| Hydrodynamic diameter | 21 nm | 62 nm |
| $r_1$ | 3.5 mg$^{-1}$ s$^{-1}$ L | 4.6 mM$^{-1}$s$^{-1}$ |
| $r_2$ | 337.8 mg$^{-1}$ s$^{-1}$ L | 143 mM$^{-1}$s$^{-1}$ |
| $r_2/r_1$ | 90 | 31 |

*Invest Radiol 2005; 40: 715-724

In the case of the commercial negative Resovist CA, the value of $r_2/r_1$ was 31 (Rohrer, M. et al in Invest Radiol 2005, 40: 715-724 and Reimer et al., in European Radiology, 2003, 13(6): 1266-1276). The high value of $r_2/r_1$ of the NPs-1A, compared to the Resovist, may be due to its high crystallinity, which increases the value of $r_2$ (Levy et al., in Biomaterials, 2011, 32(16): 3988-3999 and Salafranca et al., in Nano letters, 2012. 12(5): 2499-2503). These results confirm that NPs-1A have excellent magnetic properties for use as a contrast agent in MRI. From the values $r_1$ and $r_2$ obtained from NPs-1A (Table 2.5) and from equations 1 and 2 of Example 7, the effect of the NPs-1A is calculated on the longitudinal and transverse tissue relaxation times of a brain of an APPSwe/PS1dE9 transgenic animal. The results are summarized in Table 3.

TABLE 3

| $T1_t$ (ms) | $r_1$ (mL/mg · s) | C (mg/mL) | $T1_{obs}$(ms) | Modification of observed T1 (%) |
|---|---|---|---|---|
| 800 | 3.524 | 0.0488 | 703 | 12.09 |
| 800 | 3.524 | 0.0244 | 748 | 6.44 |

| $T2_t$(ms) | $r_2$ (mL/mg · s) | C (mg/mL) | $T2_{obs}$(ms) | Modification of observed T2 (%) |
|---|---|---|---|---|
| 80 | 337.8 | 0.0488 | 34.5 | 56.87 |
| 80 | 337.8 | 0.0244 | 48.2 | 39.74 |

As observed, the value of T1 in the presence of the effect of NPs-1A changes between 12% and 6%, while that of T2 changes between 56% and 40%, depending on the concentration of NPs-1A. These results confirm that NPs-1A are a negative contrast agent when the values of T2 vary significantly with respect to T1 values. If you compare these results with the one described for Resovist (a variation of 53% of the T2 of the tissue for a concentration of 0.1 mM) it confirms that NPs-1A is an excellent contrast agent.

Figure 14A:
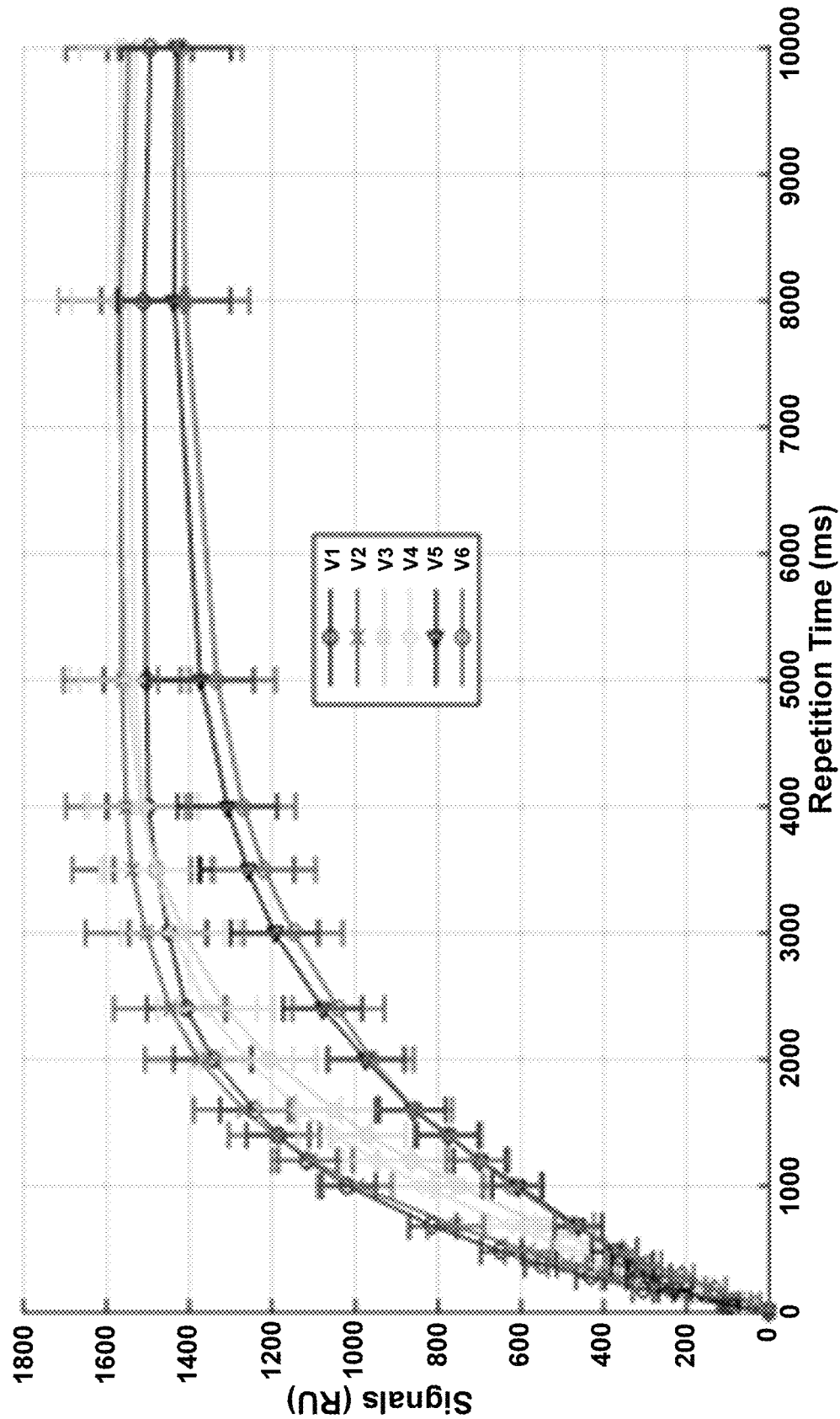
FIGS. 14A-B: shows the variations of the signal intensity of NPs-3B prepared at different concentrations. These curves are generated from the measurements made in the magnetic resonance images obtained with Spin Eco (SE) sequences.
Figure 14B:
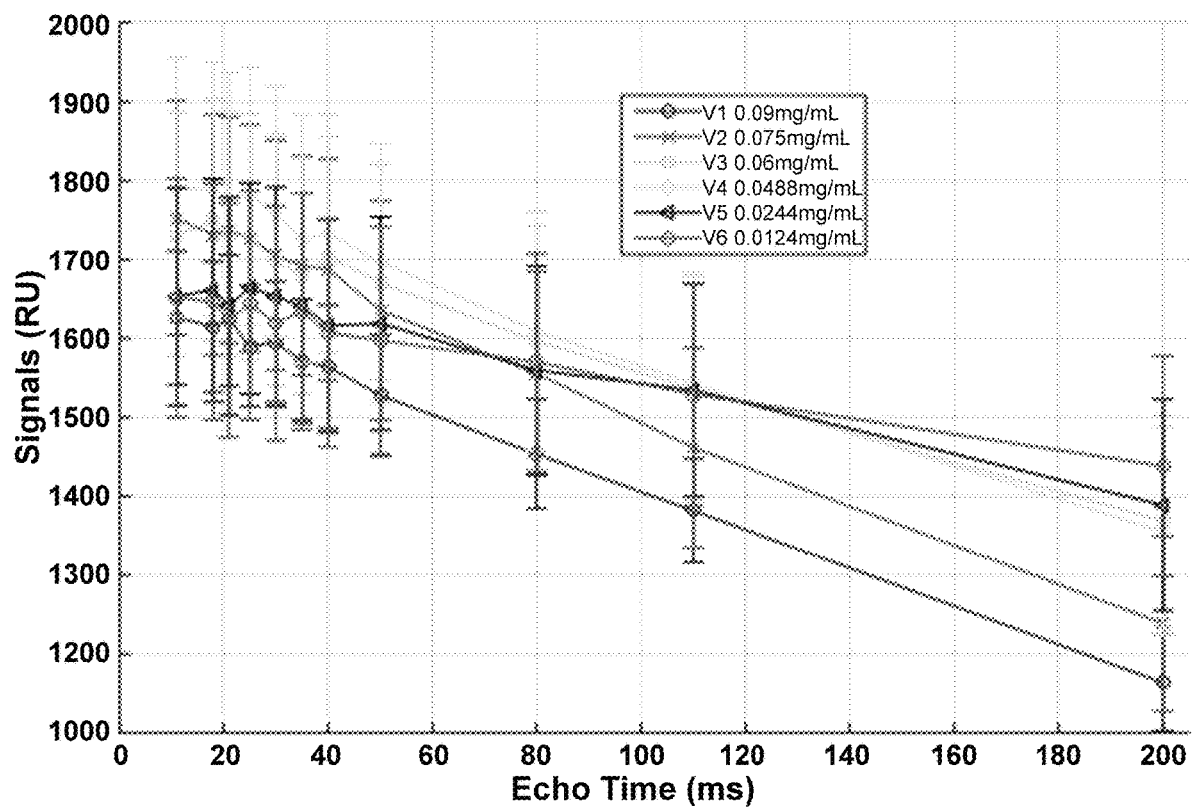

FIG. 14A shows the longitudinal relaxation curves; with an Echo Time (TE=11 ms) fixed and different values of TR, while in FIG. 14B the transversal relaxation curves are observed, with a Fixed Repetition Time (TR=10 000 ms) and different values of TE. The relaxivities values $r_1$ and $r_2$ of the NPs-3B are: $r_1$=7.74 mg$^{-1}$s$^{-1}$L and $r_2$=17.9 mg$^{-1}$s$^{-1}$L and its relation $r_2/r_1$ of 2.31. This value was compared with that described for Magnevist ($r_2/r_1$=1.19), a positive contrast agent for commercial use in MRI (Rohrer M, et al in Invest Radiol 2005; 40: 715-724). This shows that NPs-3B have excellent magnetic properties for use as a contrast agent in MRI.

From the values of $r_1$ and $r_2$ obtained from the NPs-3B, their effect on the longitudinal and transverse relaxation times of a brain tissue of a transgenic animal APPSwe/PS1dE9 was calculated. With equations 1 and 2 of Example 7, the relaxation times observed ($T1_{obs}$ or $T2_{obs}$) in the tissue are calculated as a consequence of the accumulation of NPs-3B. The modification (expressed in percentage) of the longitudinal and transverse relaxation times observed in a brain tissue of a transgenic animal APPSwe/PS1dE9 in the presence of NPs-3B is presented in Table 4.

TABLE 4

| T1$_t$ (ms) | r$_1$ (mL/mg*s) | C (mg/mL) | T1$_{obs}$ (ms) | Modification of observed T1 (%) |
|---|---|---|---|---|
| 800 | 7.743 | 0.09 | 416.5 | 47.96 |
| 800 | 7.743 | 0.075 | 444.7 | 44.41 |

| T2$_t$ (ms) | r$_2$ (mL/mg*s) | C (mg/mL) | T2$_{obs}$ (ms) | Modification of observed T2 (%) |
|---|---|---|---|---|
| 80 | 17.9 | 0.09 | 70 | 12.50 |
| 80 | 17.9 | 0.075 | 69.4 | 13.25 |

As observed, the T1 value of the tissue under the effect of the NPs-3B changes between 44% and 47% depending on the concentration, while the T2 does it between 12% and 13%. The predominant variation in the observed T1 value demonstrates that NPs-3B is a positive contrast agent. If this result is compared with the variation of 20% caused by Magnevist on tissue T1, it is concluded that NPs-3B is an adequate positive contrast agent.

Table 5 shows changes in intensity tres Regions of Interest in a healthy animal of 18 months. The zones are 1-3 in brain and cerebellum and one of reference. In zones 1-3 the contrast change was up to 22%. In the reference area, where the contrast does not reach, there were no statistically significant changes.

TABLE 5

| Zone | Before injection | After injection | Variation (%) |
|---|---|---|---|
| 1 | 802.2 | 613.6 | 23.5 |
| 2 | 1434.8 | 1487.5 | 3.3 |
| Reference | 43.7 | 45.5 | 0 |

EXAMPLES

The obtaining of the nanoparticles of this invention and their use for the diagnosis of Alzheimer's Disease is illustrated by the following examples, which should not be interpreted in any way as limiting.

Example 1: Magnetite Nanoparticles Functionalized with HOOC-PEG-NH$_2$ (NPs-1)

In a 50 mL round bottom flask under an argon atmosphere, Fe(acac)$_3$ (2.5 mmol, 0.883 g), HOOC-PEG-NH$_2$ 1000 (2.5 mmol, 2.5 g) and PEG-300 (37.3 mmol, 11.2 g) are mixed with constant stirring. The reaction mixture was heated at 160° C. for 30 min. and subsequently, at 220° C. for 2 h, with vigorous stirring. The reaction mixture was cooled to room temperature and ethanol was added. The particles were separated by centrifugation at 10 000 rpm and dispersed in DMF (1 mL) to store at room temperature. FT-IR, ν (cm$^{-1}$): 3420; 2920; 2850; 1603; 1070; 580 (ν$_{Fe-O}$).

Example 2: Magnetite Nanoparticles Conjugated with N-[4-(1-naphthylamino)-4-oxobutanoyl]-β-alanine (A); (NPs-1A)

In a 50 mL round bottom flask, A (10 mg, 31.8 μmol) dissolved in DMF (1 mL) was added. Hydroxybenzotriazole (HOBTz, 4.7 mg, 35 μmol), previously dissolved in DMF (500 μL), was added to the reaction mixture. Subsequently, 1-ethyl-3-(3-dimethylaminopropyl) carbodiimide (EDC) (8.2 mg, 52.4 μmol) dissolved in DMF (500 μL) was added. The reaction mixture was stirred for 30 min, then 200 μL of a dispersion of magnetic nanoparticles NPs-1 is added. The reaction mixture was stirred at room temperature for 4 hours. The product was magnetically separated, washed with DMF (2×250 μL) and with water (2×250 μL) and then vacuum dried over P$_2$O$_5$. The NPs-1A were dispersed in DMSO (1 mL) to store at room temperature. FT-IR, ν (cm$^{-1}$): 3370; 1645; 1018; 640 (ν$_{Fe-O}$).

Example 3: Magnetite Nanoparticles Coated with polyethylene glycol dicarboxylate (NPs-2)

In a 50 mL round bottom flask under an argon atmosphere, PEG-di-COOH-600 (0.4 g, 0.7 mmol) and 10 mL of PEG-300 (33 mmol) are mixed with constant stirring. Next, a solution of Fe(acac)$_3$ (0.18 g, 0.51 mmol) in 2.5 mL PEG-300 was added. The reaction mixture was heated at 160° C. for 30 min. and subsequently, at 220° C. for 2 h, with vigorous stirring. The reaction mixture was cooled to room temperature and ethanol was added. The particles were separated by centrifugation at 10 000 rpm and dispersed in DMF (1 mL) to store at room temperature. Mass of the product obtained: 200 mg. FT-IR, ν(cm$^{-1}$): 3420; 2924; 1626; 1412; 1096; 571

Example 4: Magnetite Nanoparticles Coated with polyethylene glycol dicarboxylate (NPs-2) Conjugated to N1-(2-aminoethyl)-N4-(1-naphthyl)succinamide (B) (NPs-2B)

In a 50 mL round bottom flask immersed in an ice bath, 200 μL of NP-2 (dispersed in DMF (1 mL) of Example 3) and a solution of HOBTz (4.7 mg, 35 μmol) in DMF were added (500 μL). Then a solution of EDC (8.2 mg, 52.4 μmol) in DMF (500 μL) was added. The reaction mixture was stirred for 30 min to add a solution of 3 (10 mg, 35 μmol) in DMF (500 μL) and then stirring at room temperature for 48 h. Finally, the conjugated nanoparticles (NPs-2B) were magnetically separated, washed with DMF and water (2×250 μL, each one) and dried in a vacuum under P$_2$O$_5$ for 24 h. The particles were dispersed in DMSO (4 mL) and thus stored at room temperature. Mass of the product obtained: 40 mg. FT-IR, ν(cm$^{-1}$): 3432; 2920; 1592; 1397; 616

Example 5: Gadolinium Oxide Nanoparticles Coated with polyethylene glycol dicarboxylate (Gd$_2$O$_3$-PEGdicarboxylated) (NPs-3)

In a 50 mL round bottom flask, equipped with a reflux condenser, 3.45 g (5 mmol) of GdCl$_3$×6H$_2$O were dissolved in 25 mL of PEG (Mn=400), at 100° C. with stirring. To this solution was added a solution of NaOH (0.6 g, 15 mmol) in 10 mL of PEG (Mn=400). The reaction mixture was heated at 180° C. for 4 h, with constant stirring. Then, the temperature was lowered to 80° C. to add 8 mmol (4 mL) of PEGdicarboxylated (PEGD, Mn=600) and then, it was again heated at 180° C. for 4 h, with constant agitation. The reaction mixture was cooled to room temperature to add 500 mL of distilled H$_2$O. The colloidal suspension was stirred for 10 min and then allowed to settle until the sedimentation of the particles (about one week). The supernatant liquid was decanted and the solid was dried under vacuum in a desiccator over P$_2$O$_5$. Mass obtained from NPs-3: 893 mg. FT-IR, ν(cm$^{-1}$): 3295; 1580; 1525; 1431; 1401; 1301; 1006.

Example 6: Gd₂O₃-PEGdicarboxylated Nanoparticles (NPs-3) Conjugated with N1-(2-aminoethyl)-N4-(1-naphthyl) succinamide (B)) (NPs-3B)

In a 25 mL round bottom flask, 5 mg of Gd₂O₃-PEGD were dispersed in 4 mL of DMF and an EDC solution (40 mg, 0.26 mmol) in DMF (4 mL) was added. The reaction mixture was cooled in an ice bath and HOBT (20 mg, 0.13 mmol) and 3 (40 mg, 0.14 mmol) were added in stepped time of 30 min, between them. Then, it was stirred at room temperature for 2 days and centrifuged at 10 000 rpm for 30 min to remove the supernatant fluid. The solid was washed with ethanol (10 mL×3) and dried under vacuum in a desiccator over P₂O₅. Mass obtained from NPs-3B: 2.7 mg. FT-IR, ν(cm⁻¹): 3454; 2933; 2870; 1650; 1498; 1387; 1255; 1095.

Example 7: In Vitro Characterization of the Magnetic Properties of NPs-1A and NPs-3B The contrast agents (CA) affect both the T1 and T2 observed ($T1_{obs}$, $T2_{obs}$) in the tissues in which it accumulates. Equations (1) and (2) describe this phenomenon (Haacke E M, et al., in Magnetic Resonance Imaging Physical Principles and Sequence Design, 1999. United States, New York).

$$R_{1obs} \equiv 1/T1_{obs} = 1/T1_t + r_1 * C \quad (1)$$
$$\equiv R_{1t} + r_1 * C$$

Being:
- C—Concentration of the CA (mM or mg/ml, depending on the availability of the substance)
- $R_{1obs}$—speed or relaxation rate observed (s⁻¹). It is the relaxation rate of the tissue modified by the CA with a concentration C.
- $T1_{obs}$—observed T1 (ms)
- $T1_t$—T1 of the tissue (ms)
- $r_1$—longitudinal relaxitivity (mM⁻¹s⁻¹)

In a similar way, it is proposed for T2:

$$R_{2obs} \equiv 1/T2_{obs} = 1/T2_t + r_2 * C \quad (2)$$
$$\equiv R_{2t} + r_2 * C$$

Being:
- $R_{2obs}$—speed or relaxation rate observed (s⁻¹). It is the relaxation rate of the tissue modified by the CA with a concentration C
- $T2_{obs}$—observed $T_1$ (ms)
- $T2_t$—T1 of the tissue (ms)
- $r_2$—Transverse relaxivity (mM⁻¹s⁻¹)

The improvement in the intensity of the tissue signal is not only determined by the relaxitivities $r_1$ and $r_2$ of the contrast agent. But also by the concentration levels of this in the tissue. In the limit case of high concentrations can lead to signal saturation and loss of contrast (Elster A D et al in Radiology 1990; 174: 379-381). For this reason, at lower concentrations, better results are obtained.

Concentration values of the solutions of the NPs-1A and NPs-3B nanoparticles used in relaxivity measurements.

| tubes | NPs-1A (mg/mL) | tubes | NPs-3B (mg/mL) |
|---|---|---|---|
| 1 | 0.012 | 1 | 0.09 |
| 2 | 0.024 | 2 | 0.075 |
| 3 | 0.048 | 3 | 0.060 |
| 4 | 0.072 | 4 | 0.0488 |
| 5 | 0.096 | 5 | 0.0244 |
| 5B | 0.120 | 6 | 0.0124 |

Example 8: In Vivo Study. Modification of T1 and T2 Relaxation Times in Brain Tissue with Amyloid Plaques, in the Presence of NPs-1A The in vivo study was performed with 5 mice (APPSwe/PS1dE9 transgenic mice, 12 months) and with 3 healthy mice of the same age. Mice were anesthetized (5 mL/kg body weight) with a mixture of 100 mg/mL ketamine and 10 mg/mL xylazine in phosphate buffered saline (PBS). The suspension of NP-1A was diluted with PBS (pH 7.4) at a dose of 5 mg/kg Fe/kg body weight immediately before injection. A total of 100 μL of diluted NP-1A was injected through the tail vein.

In-vivo measurements were made in the brain of mice to quantify the variations in intensity as a result of the administration of CA. The quantification of contrast variation was carried out according to the equation:

$$\text{Contrast} = 100 * (\text{Area}_{Before} - \text{Area}_{After})/\text{Area}_{Before}$$

Where $\text{Area}_{Before}$ is the intensity of the area before the administration of the CA and $\text{Area}_{After}$ is the intensity of the area after the administration.

Figure 15A:
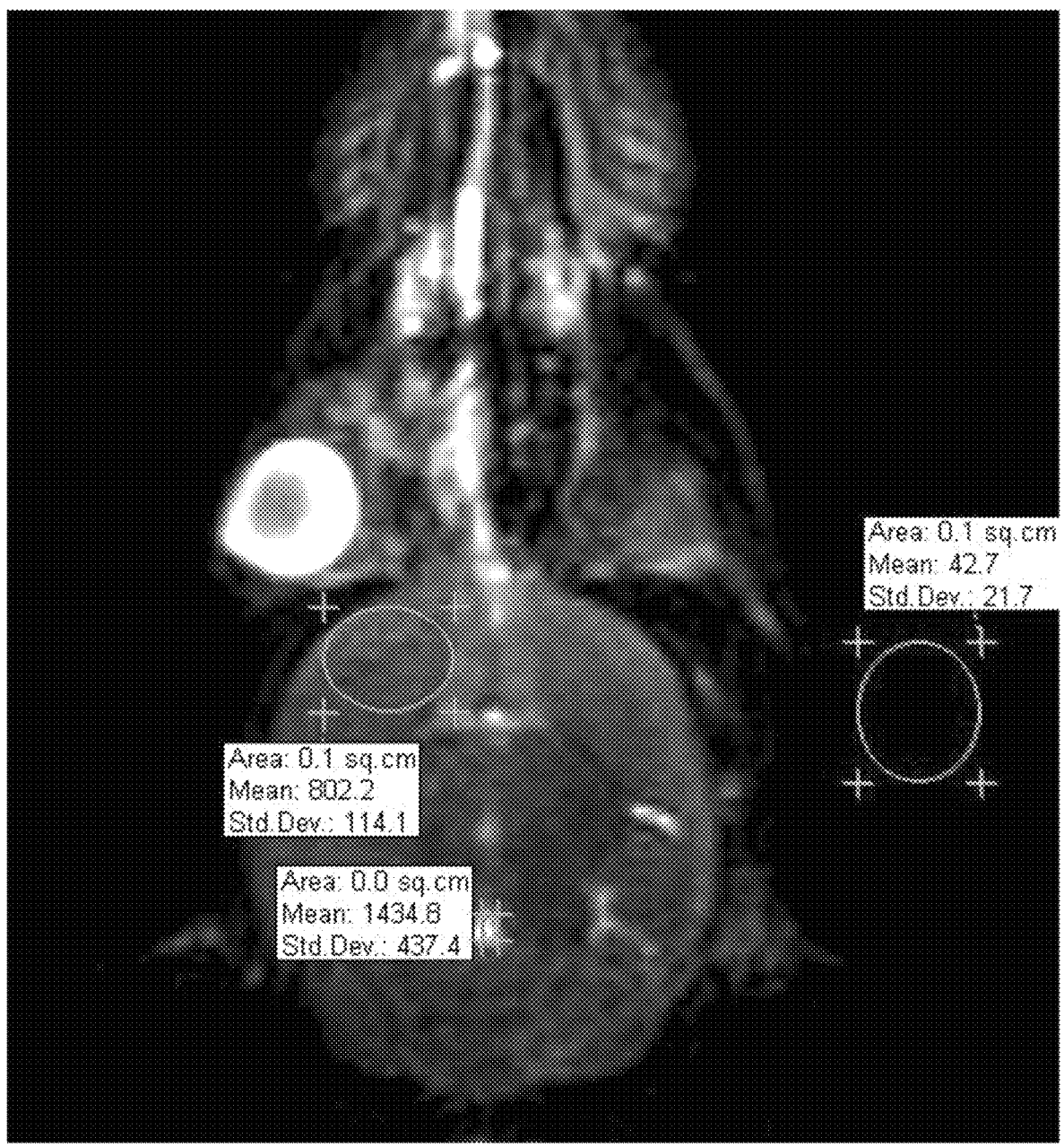
FIGS. 15A-B: intensity measurements in different areas are presented in the transgenic mouse brain images. On the left the intensities measured before contrast administration in four zones (including reference). On the right the intensities measured after the administration.
Figure 15B:
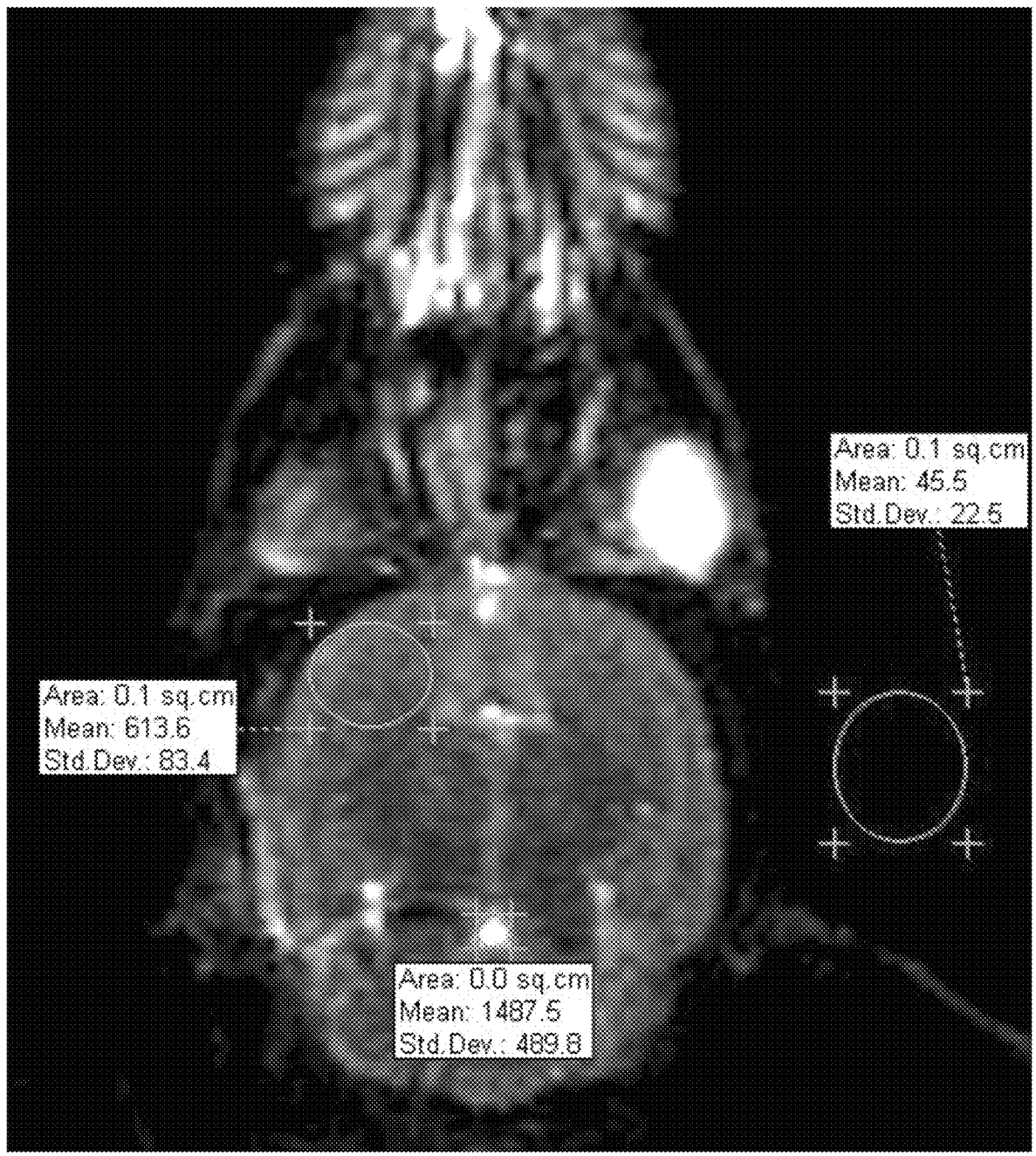

In FIG. 15, images of the animal are observed before and after the injection of CA. These are coronal sections weighted in T2 with a spin echo sequence (TR/TE 4000/80) and a spatial resolution of 180 μm.

Table 7 shows the in-vivo effect of the application of NPs-1A. Contrast changes were achieved between 17 and 22%. This is considered a good result that corroborates NPs-1A as a negative agent because it decreases the intensity of the image.

NPs-3B is administered in a similar group and increases in signal intensity of about 25% are obtained. In this way it is corroborated that this new compound is a positive contrast agent.

Example 9: Histological Evaluation of the Detection of Plaques in the Brain Tissue of Mice Once the imaging study was completed, the animals were deeply anesthetized and perfused with a solution of 4% paraformaldehyde in 0.01 mol/L PBS pH=7.2. After the mice died, their brains were removed, washed with saline, dried, cut in half and embedded in paraffin. Then, the brains were sectioned into 4 mm thick slices using a microtome. The sections were dewaxed, hydrated in distilled water and treated with 70% formic acid for 30 minutes. The sections were serially stained to locate the β-amyloid deposition. Cuts were treated with 3% $H_2O_2$ for 30 minutes to eliminate residual peroxidase activity, and rinsed again with 0.01 mol/L PBS (pH=7.2). Sections were incubated overnight at 4° C. with an anti-Aβ1-42 monoclonal antibody (SIGMA, USA) at a 1:1000 dilution. The slides were then rinsed with 0.01 mol/L PBS (pH=7.2) and were first incubated with a secondary antibody (SIGMA, USA) for 30 minutes and, second, with an avidin-biotin complex (SIGMA, USA) for 30 min., At room temperature. For the staining, diaminobenzidine was used for 10 min as a chromogen. The sections were contrasted with Harris's haematoxylin and mounted in aqueous medium. Brain slices from healthy mice were taken as negative controls and received the same treatment. The images were visualized with the Olympus BX51 microscope camera (Japan) (FIG. 15).

Figure 16A:
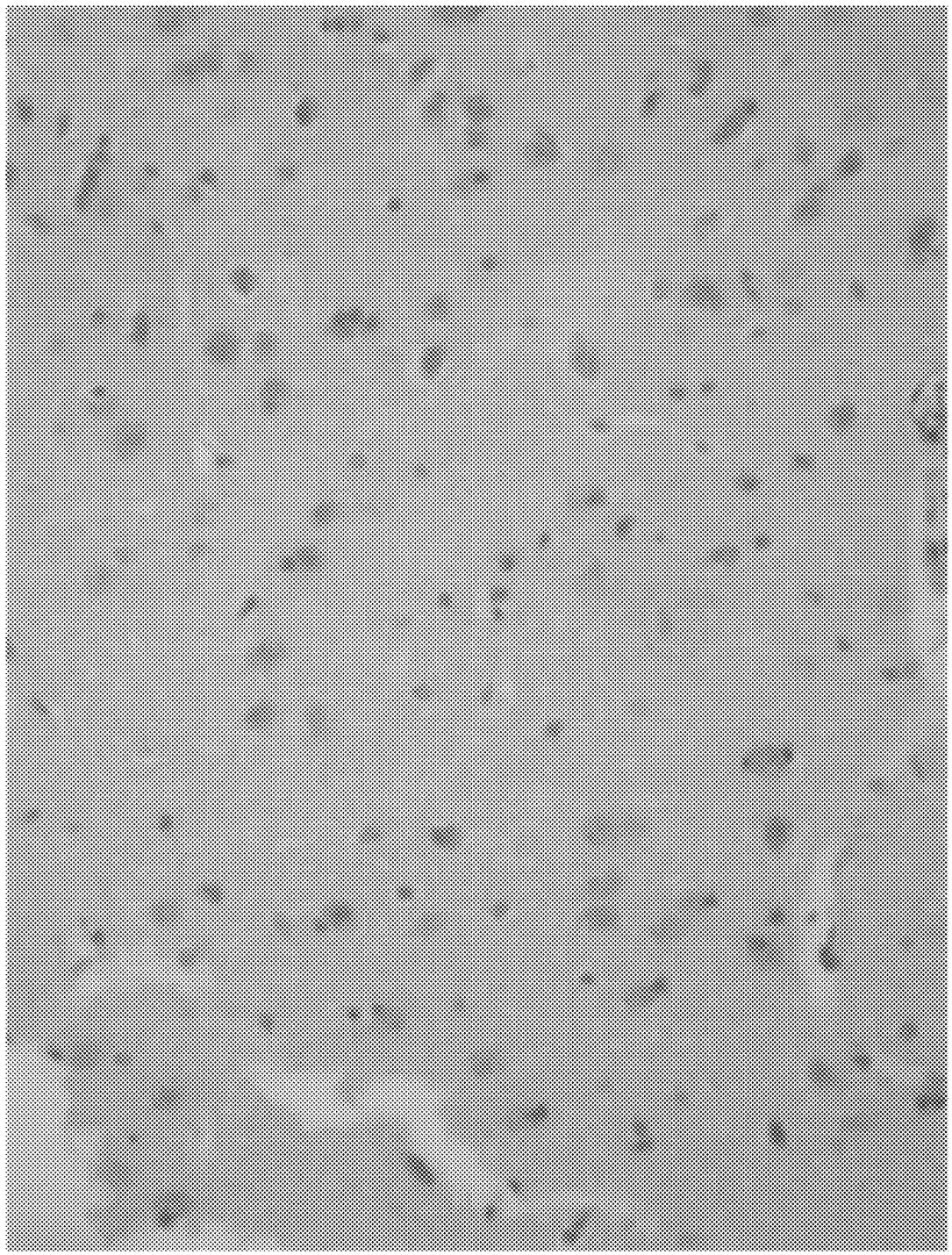
FIGS. 16A-B: representative microphotographs of the prefrontal cortex corresponding to healthy animals and transgenic APPSwe/PS1dE9 mice (scale bar=200 μm) are presented.
Figure 16B:
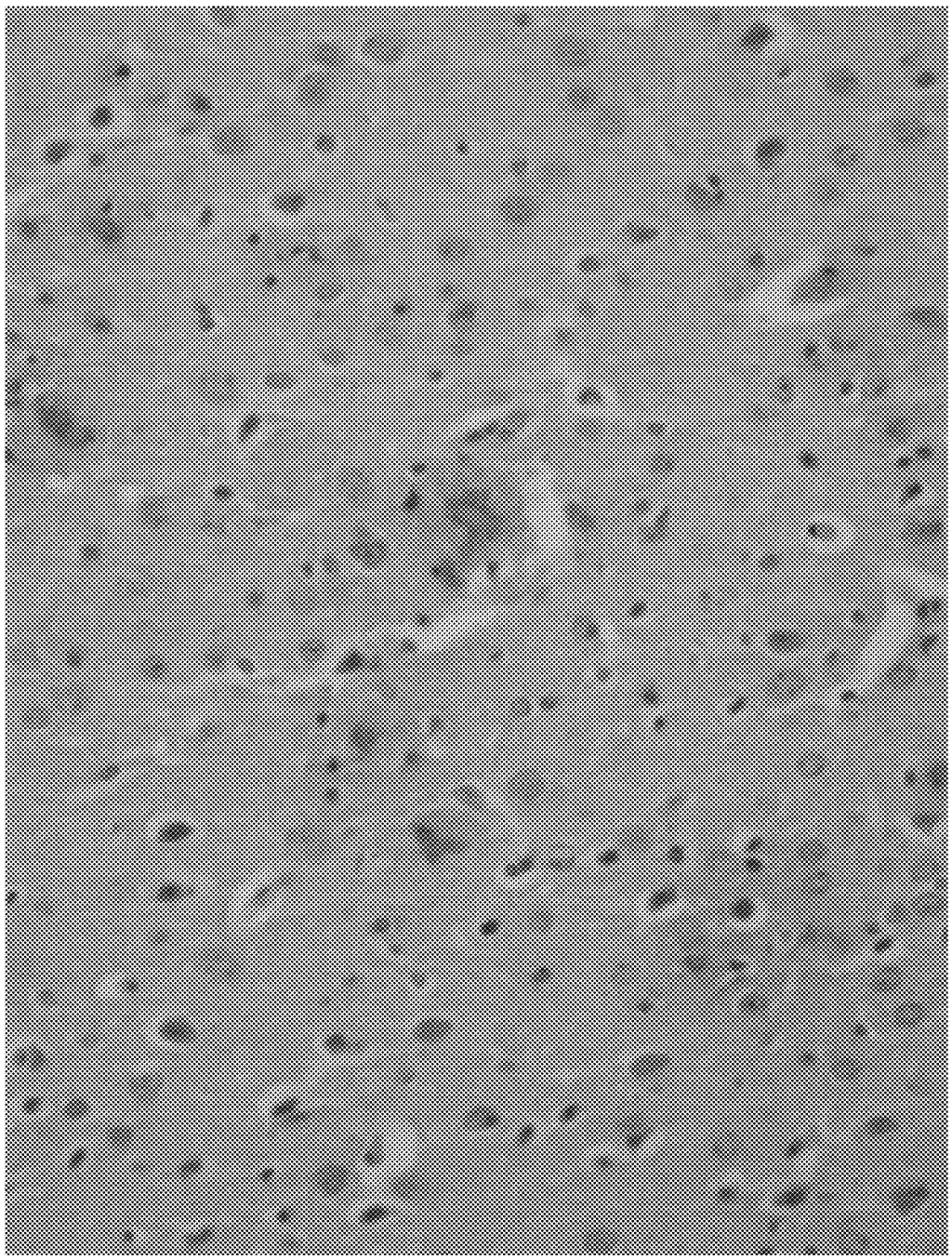
Figure 17:
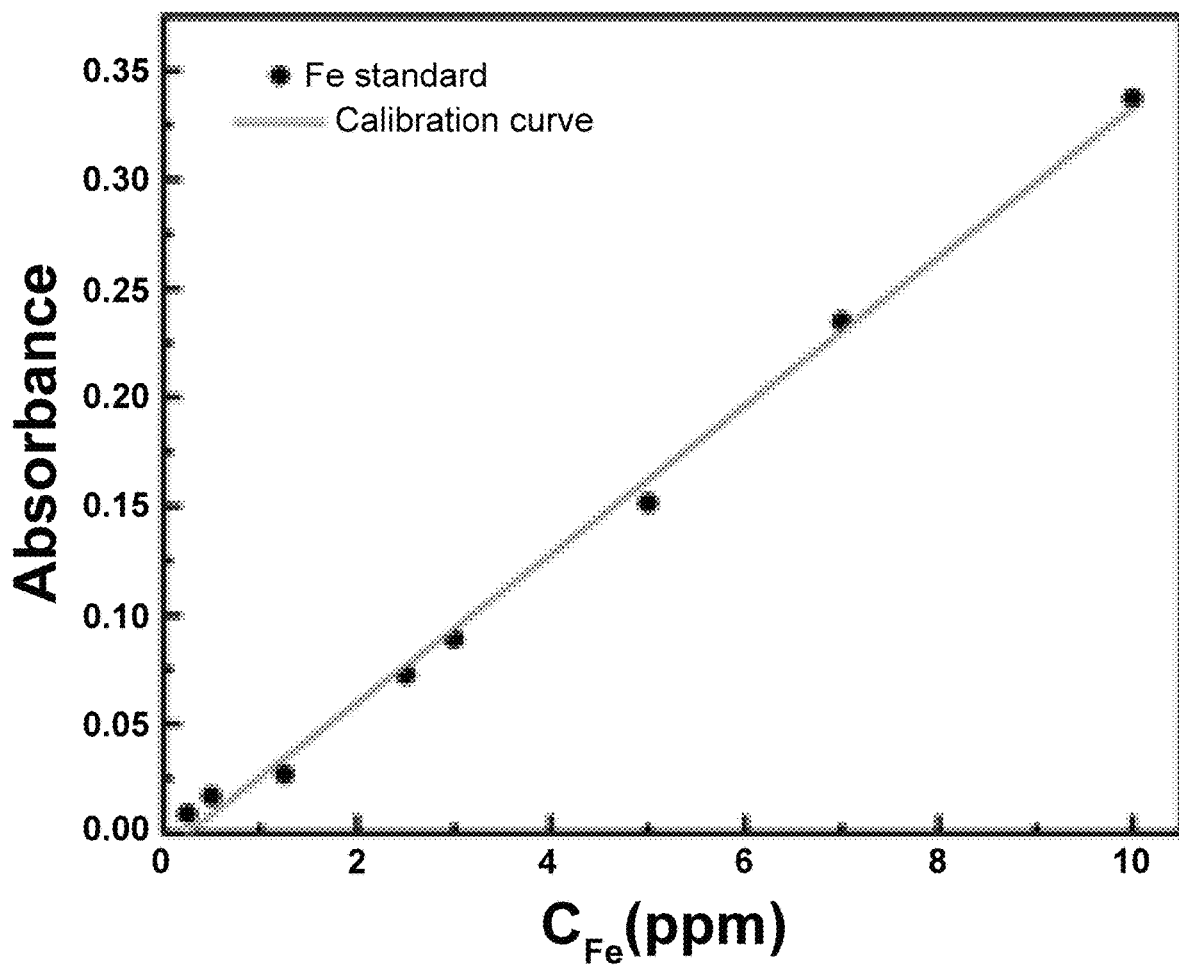
FIG. 17: shows an Fe calibration curve and linear adjustment used for Table 1.

FIG. 16A shows pre-frontal cortex tissue of a healthy mouse C57. No β-amyloid plaques are observed. FIG. 16B shows pre-frontal cortex tissue of transgenic mouse 2×Tg (APP/PS1), at 18 months. β-amyloid plaques are observed.

The invention claimed is:

1. A magnetic nanoparticle related to the agglomerates and β-amyloid plaques for the diagnosis of Alzheimer's disease by magnetic resonance imaging, characterized by compounds of Formula I comprising a metal oxide core coated with a multifunctional organic layer, wherein said organic layer is conjugated with a naphthyl compound,

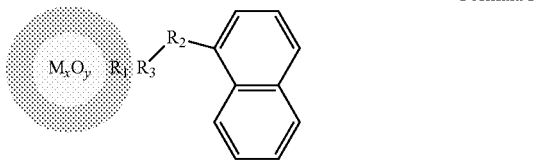

Formula I wherein:
R$_1$: is an organic coating to the metal oxide core, of polymeric type selected from the group polyethylene glycol (PEG), amino-PEG, PEG-carboxyl acid, amino-PEG-carboxyl acid, PEG-di carboxyl acid, PEG-polylactic acid, and PEG-polylactic-co-glycolic acid;
R$_2$: is —NHCO-alkylenyl-C(O)NH-alkylenyl-R$_3$;
R$_3$: is —COO—, —CO—, —NH, —O—, —S—, —NH-alkylenyl-NH—, —NR$_4$—CSS—;
R$_4$: is —H, —CH$_3$, —CH$_2$—CH$_3$, —CH$_2$CH$_2$CH$_3$, and
M$_x$O$_y$: is iron oxide (Fe$_3$O$_4$/γFe$_2$O$_3$), gadolinium oxide (III), manganese oxide(II) or copper(II) oxide;
wherein the naphthyl compound is selected from the group: N1-(2-aminoethyl)-N4-(1-naphthyl)succinamide, N-[4-(1-naphthylamino)-4-oxobutanoyl]-β-alanine, 6-{[4-(1-naphthylamino)-4-oxobutanoyl]amino}hexanoic acid, N1-(2-aminobutyl)-N4-(1-naphthyl)succinamide, N-(2-hydroxyethyl)-N'-1-naphthyl succinamide, N-(3-mercaptopropyl)-N'-1-naphthysuccinamide, N-{2-[(2-aminoethyl)amino]ethyl}-N'-1-naphthysuccinamide and (2-{[4-(1-naphthylamino)-4-oxobutanoyl]amino}ethyl) carbamodithioic acid sodium salt;
wherein the alkylenyl term in R$_2$ and R$_3$ is selected from the group consisting of ethylenyl (—CH$_2$CH$_2$—), butylenyl (—CH$_2$CH$_2$CH$_2$CH$_2$—) and hexylenyl (—CH$_2$CH$_2$CH$_2$CH$_2$CH$_2$CH$_2$—);
wherein the conjugated, functionalized and coated magnetic nanoparticle is capable of, when it is administered to a mammal, crossing the blood-brain barrier and specifically binding to the agglomerates and β-amyloid plaques present in brain tissue;
wherein, with the nanoparticle bound to the agglomerates and β-amyloid plaques in the brain tissue, hypo- or hyper-intense signals are observed in the region of interest through magnetic resonance imaging.

2. The magnetic nanoparticle related to the agglomerates and β-amyloid plaques of claim 1, wherein the organic coating R$_1$ of the metal oxide core is bonded to R$_3$ via a terminal functional group selected from the group consisting of —SH, —OH, —NH$_2$, —NCS, —COOH and its esters of N-hydroxysuccinimide and —Br.

3. The magnetic nanoparticle related to the agglomerates and β-amyloid plaques of claim 1, wherein a hydrodynamic radius of the coated nanoparticles, functionalized and conjugated with the naphthyl compound is less than 150 nm.

4. The magnetic nanoparticle related to the agglomerates and β-amyloid plaques of claim 1, wherein a hydrodynamic radius of the coated nanoparticles, functionalized and conjugated with the naphthyl compound is between 100 and 5 nm.

* * * * *